(12) United States Patent
Selvaraj et al.

(10) Patent No.: US 7,745,605 B2
(45) Date of Patent: Jun. 29, 2010

(54) BNLEA3-1 PROMOTER

(75) Inventors: Gopalan Selvaraj, Saskatoon (CA); Jun Huang, Saskatoon (CA); Raju Datla, Saskatoon (CA)

(73) Assignee: National Research Council of Canada, Ottawa, Ontario (CA)

( * ) Notice: Subject to any disclaimer, the term of this patent is extended or adjusted under 35 U.S.C. 154(b) by 457 days.

(21) Appl. No.: 11/907,130

(22) Filed: Oct. 9, 2007

(65) Prior Publication Data

US 2008/0244793 A1 Oct. 2, 2008

Related U.S. Application Data

(62) Division of application No. 10/387,384, filed on Mar. 14, 2003, now abandoned.

(60) Provisional application No. 60/364,115, filed on Mar. 15, 2002.

(51) Int. Cl.
*C12N 15/82* (2006.01)
*A01H 5/00* (2006.01)
*A01H 5/10* (2006.01)

(52) U.S. Cl. .................. 536/24.1; 800/298; 435/320.1
(58) Field of Classification Search ................. None
See application file for complete search history.

(56) References Cited

U.S. PATENT DOCUMENTS 5,723,765 A * 3/1998 Oliver et al. ................ 800/268

OTHER PUBLICATIONS

NDong et al., Plant Physiol. (Jul. 2002) 129(3): 1368-81.
Whisstock et al., Q Rev Biophys. (Aug. 2003) 36(3): 307-40.

* cited by examiner

*Primary Examiner*—Cynthia Collins
(74) *Attorney, Agent, or Firm*—Hans Koenig

(57) ABSTRACT

Late embryogenesis abundant (Lea) proteins accumulate in maturing seeds after many of the storage compounds have been synthesized, and they are considered relevant to maturation. We report here the molecular organization and expression of BnLea3-1, a novel Group 3 Lea gene from *Brassica napus*. BnLea3-1 contains a coding region of 798 bp, sharing 84.4% homology at the amino acid level with Lea76 of *B. napus*. Two tandem 11-mer repeats are truncated from the coding region of BnLea3-1, compared to the 13 conserved 11-mer repeats of Lea76. Substitutions of consensus residues are found at various positions within the 11-mer repeats. A 1561 bp 5' flanking promoter fragment of BnLea3-1 fused to *E. coli* β-glucuronidase (GUS) coding region conferred seed-specific GUS expression in stable transgenics of *B. napus*, tobacco and in transiently-transformed pea. A −137 bp minimal promoter preceding the first transcription start site, identified through progressive deletions from the upstream was sufficient for basal GUS expression in the seeds and in leaves treated with ABA. Deletion studies indicate the presence of enhancing elements located between −137 bp to −742 bp and suppressing elements located between −742 and −1561 bp. BnLea3-1 expression in seeds precedes that of Lea76. Unlike other Group 3 Lea members including HVA1 and Dc3, BnLea3-1 is active in seeds and responsive weakly in vegetative tissues to ABA and methyl jasmonate (MeJA) but not to stress treatments. Possible functions of BnLea3-1 and another member of the Group 3 Lea family BnLea3-2 in embryo development is discussed.

12 Claims, 16 Drawing Sheets

(A)

```
M  A  S  N  Q  Q  S  Y  K  A  G  E  T  R  G                    15
K  T  Q  E  K  T  G  Q  A  M  G  A  M  R  D                    30
K  A  E  E  G  R  D  K  T  S  Q  T  A  Q  T  A  Q  Q  K  A  Q  E   52
T  A  Q  A  A  K  D  K  T  S  Q  T  A  Q  T  T  Q  Q  K  A  H  E   74
T  T  Q  A  T  K  D  K  T  S  Q  A  A  Q  T  T  Q  Q  K  A  H  E   96
T  T  Q  A  A  K  D  K  T  S  Q  A  A  K  T  A  Q  E  K  A  H  E  118
T  K  D  K  T  G  S  Y  M  S  E  T  G  E  A  I  K  Q  K  A  Q  N  140
A  A  Q  Y  T  K  E  T  A  Q  E  A  A  Q  Y  T  K  E  T  A  E  A  162
G  R  D  K  T  G  G  F  L  S  Q  T  G  E  Q  V  K  Q  M  A  M  G  184
A  A  D  A  V  K  H  T  F  G  M  A  T  E  E  D  K  E  H  Y  P     206
G  T  T  I  T  T  T  G  T  T  R  T  T  D  P  T  H  H  T  Y  Q  K  228
E  V  M  I  A  R  E  L  C  N  V  S  F  L  L  F  L  Y  C  L  V  W  250
S  F  D  F  S  V  S  L  F  V  I  S  V  V  S  L  C  L  END          269
```

SEQ ID NO: 37

(B)

BnLea3-1
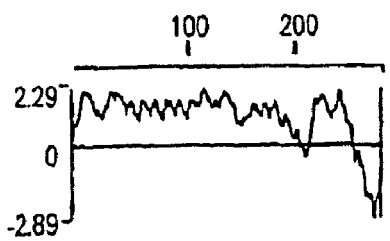

BnLea3-2
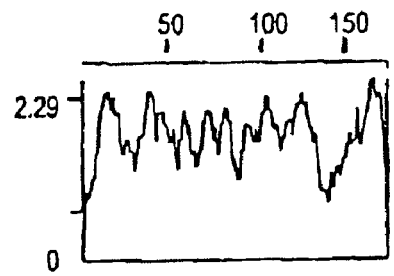

BnLea3-3
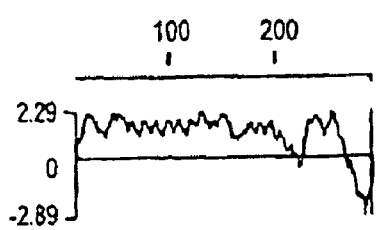

BnLea3-4
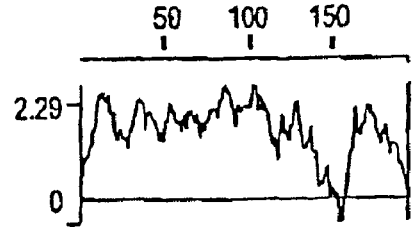

Fig. 1

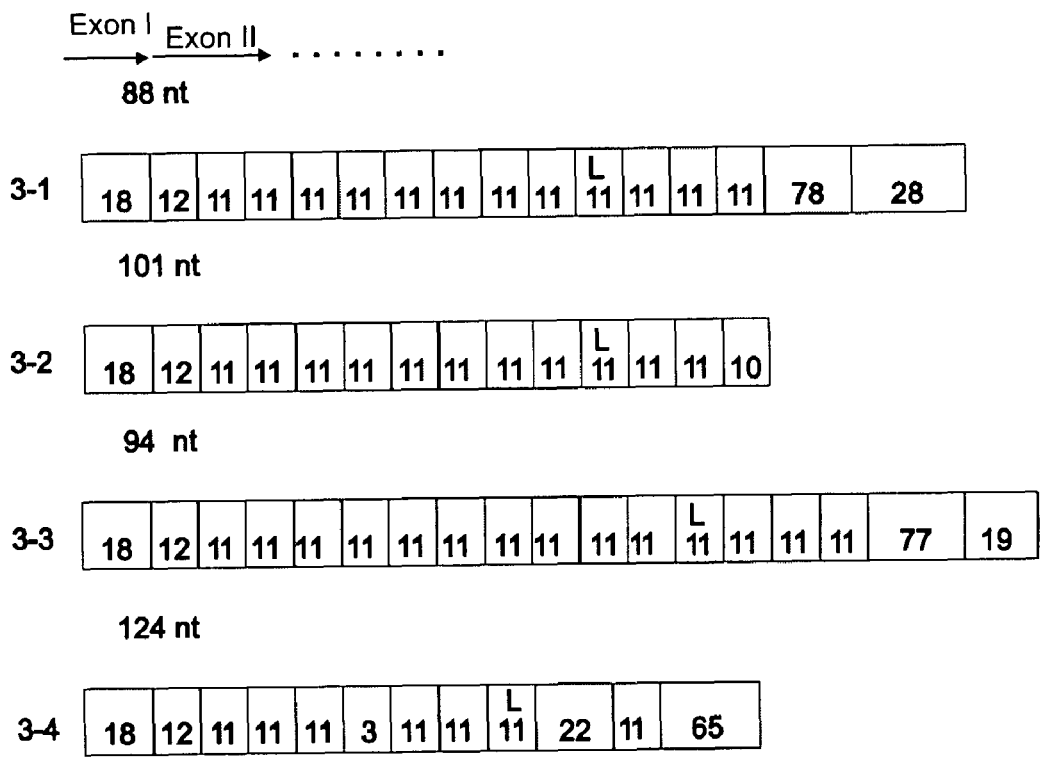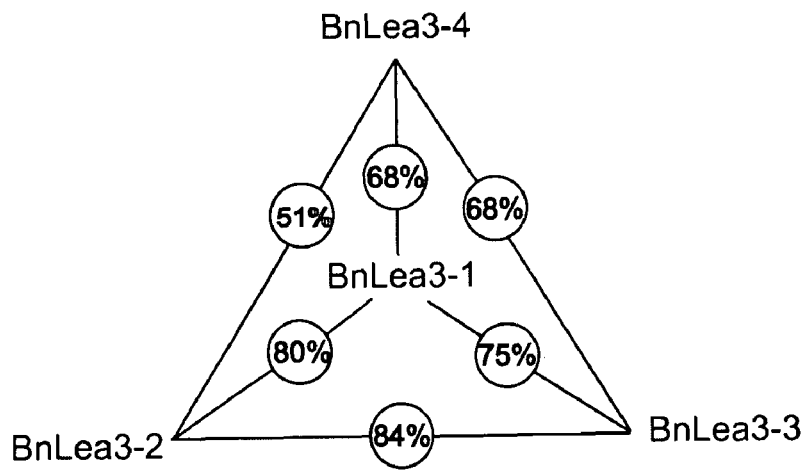
Fig. 2

SEQ ID NO: 1 and SEQ ID NO: 37

Fig. 6A

```
GTCATGGAATTCTTTGTTAGATTAAAATATAAATCTTAAATAAATTGTCCATAAATTCGTATAAAATATATT      -1825
TTCACATGTTTTTTTTAAAACTAGGAAGAGTTTGGATCTTGAGCCCTAGTCTAGCTCCAGAGTTGGGATTT      -1753
TCACTACTTTTGTTAAGAGTTCTTCTTAAGTATGAATATACCCATGTGTCATATTCTTCATTTGTTCTCATG     -1681
TTTATGTTTCAGTTCATATTCTTCATTTGTACCAATCCAGGTGAAGTAGAAGATATTATATTTGTTCGATTC    -1609
TCTAGCTTGTTTAAATTTACTAGCCGGCTACTGGTGCTGGTTTGTGTTTGATACATGGTTGAAGGACTCATC    -1537
TCTTTTTTACCGTTATCGTATATATCATAAGTAGTGGCGTCAACTCGAATGTTACCAACGTTTGCTAATTTT    -1465
TCGTTTGCGGCGCGTCTATTTCTCACGTACCTGATAGAGTATTTATATAATTTATAGAAAAGCATTGTATCC    -1393
CCATTCGATTAAACATGGTAAGTATTTTCATTGGCTAGTTGTCACACGTATAACAAGGCTAATTAATTATAT    -1321
GTGGATGTGAATACATAGTTCAAACTAAACCTCGAAGTAGATGAGATCAATTCAATTCAAAAAACTTTAGTA    -1249
AGACGGAGACCGGGACTTCTCTCTCTCCTCTGTGAGATGAGTGTTGAAGCTTTTCGCCCGGTGCTCTATCTT    -1177
TGCTTTTGATTCTTGTTTTCTTGGGCTTTGAATCCGGGAAGCCGTTTGCTCTTTAGTTCTTACGCAGGCTTC    -1105
GCTAGTTCTGTTTCCGGGAGAAGGAGGCTTCCTTGGCTCCGTTTCTCGCCGGCTTACGATTCCGAGGTGTGG    -1033
AGGCTCCGAGCCTAGCGCCGTTGGCTTTGATTATCACCCCTTTCCTCAAGGGTGTGACTTCAGCTTTGCTCG     -961
TGATTTATGTGCTCTTGGTTTAGTTCCCTCTGAAGAGATCTCGAATAGATCGAATGTTTCTCTTCGATGGTG     -889
TTGACATCAAACAAGAGGAGGTGTGGGATTACTTTAATCCCGTGATTGGCGGCTTGGTGGCTCAGGATGAGC     -817
TCTCGAAGTGGTTCGATGGAAGCTCTCCGGAGAAGAGCTCAGCCGTGGATGGTGGTCGCGATGTCGGGTATG     -745
GTTCCGGTGATGAGTTGCATGTTCCCTCCGGCGATGGAGGCAGGAGAAGGGGTTTGGCGACACGTGTGCCT      -673
CGCAGTTGAGGTCTCAACACGTGGGCCGTTGTGCTGTCGTTTGGGACGGTGGCATCTTTTTGGGCTTTGTT      -601
GGGCCGGGATTTTAGACGCTCCTTTTGTTGGTTTTTTTTTTAGGTTTTAGGTCCATCTTGGTCTTTCGCTGT     -529
AATGGTTGTATGGGGTTTGGTTCTGTTGGACTCTTTTTATAATAATAATAATAATAGATGGAAAAAAAAAAA    -457
AAAAAAAAAACCTCGAAGTTGTCTGGATACTTCTATATTTTAAGTTTCGATTTCAGCGAACTGGTGACCAAG    -385
TGATGTTTGATTATTTGACAATGTCACGGAAACATGCATGTAACAACCGATACAAATGGTCAAAACTTAACA    -313
TAGCCATATTGATATTATAACATGCGGCGCCACACTTATGGTGTTGACACGTAGCAAGCATCTTCAGTTAAC    -241
CATAACGTGTCGCAACCACACAGGATAACACGTACAAGATCGAGAAACCGCATACTAAACACTGGCAAACTA    -169
CAACACCCATACTCACTAATTTAATTAGCTTTTAATCTCAACACACCACGCAGCTATACACGTGTCTTCTAT     -97
GCCAACACGTGCCTTGTTCTCAAACCGACCAAGACACACTATAAATGTCTCGATGGTTTGGAGAGACAATAC     -25
ACATTTTCTACACAGCAACAAACAGTTAAGAAAAAGCTTTAACTTTCATTTCATATTTGCTCATTTGAAGA      68
AAAGAAAAATG → ORF
```

SEQ ID NO: 2

FIG. 6B

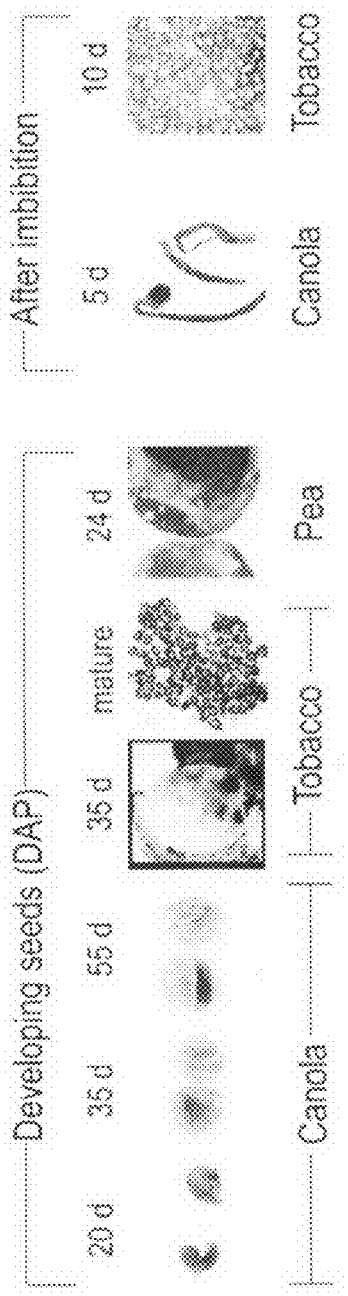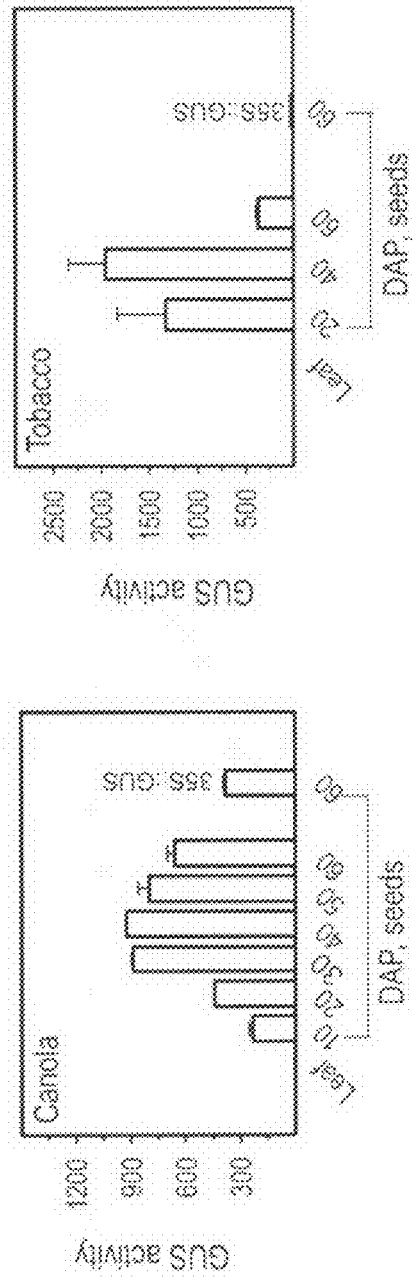
Fig. 7

X91919=At1g52690(F6D8.9)
X91912=At3g15670(CAA63006)

5'--
TTTCCAATATGGATTTTGGAAAAACCGGGGAAAATGTTATTAACCATTTTAACC
AAAAaTATATGGGCTAAACATATGGGGAATTAAACTTAACCGGAATGTAAGTGG
GGATGCCTCAACTATGGTCGTTTATGGGACAATATaACCCTTGGAGAACATATTA
TTTATTTGTTTCATGGTCACGTTTCAATTCGATCATGTTTTGCATGGACTATTATT
AGTACTCGTCACAGTAAAAGCTGAAGATATgGTATAGAACAGTAGAACCCCAAA
AGAAATCGTATAGATCAAACTGTTACTTTCTGTAAAAAAAATCCGTTAAAAAAA
TGATTTTGCATTTCAGAATCACTAAAAAGAAATCTTAAATCTAATTTAGATAAACG
GTAAATTGTGTGGTTTATAAGGAATATCAGCAATGATAAAAAGTGAAAACAATAC
GGAATTTCTCAATTGTTGTGTATTTTATTGATTTAATATATATATATATATATATAT
ATAATTTTTTTTTTTTTTGAACTATaAAACCATCGATTATGAGACAAATATTGTAA
TTTGAGTTTCGCACAAATAAAAGAGTACTCCTCTTAGTTTTTCTCTTATATATTTA
TTATTTTCATCTACTTATAGATTATGCAAATGATTCTCAATGATAATGCTATAAAAT
GGTTGTAGATAAAGGATAAATAAGGGAGGAAGAATCTGGAGTATATAAAATAGGG
AAAAATATATAAAACTTACTGCCTATTGGTAAACATTTTGAGAAATATGGGATCAT
TAAAGTTAAAGTTAAGCTGCAACTGTGGATTCTGAHTCATATGCaGaCTGTGaTTGA
TACGTTGTTGaAGTAACTCAccTTTTGTTTTTTTTTCTCTGTTATATATAGTATCATAT
GTATTGCTGCCATTCAAAATTTACTAAATTGTTGTTAATTTTCTATATCATCGTCAT
CTGGCGCCATTCGAATTTTACTACATATATGTTGTTCTAACATTTGTGCTAATATTT
TCAACGTGCATCAGTCTGGGTTGTATTTCATTGGCTAGTTGTCACACATCGAACAA
GGCTAATCATATGTGGAGGTGAGTACGTAGTTCAAGGACTAACCTCGAAGTTGCTC
GTTTTCGGGAATACTTTTATATTATCAATTTTGATTTCAaAACGCTAAAGAGTATTTT
AATGTACTATCTCTAAGTGATGTTTGATTGTTTGACACGGTTACGGAACATGCACGT
AACGACCGATACACAATGAAGAACAAAAATTATGATAAGCCATATTGATAGTAATA
TATTATAACATGCGGTGAACGACACTTCTTGTGTCACCACGTTATCAAGCATCCTTTC
AATCAACCATGATGTTGTTCGCAACCACAGAAGAACAACACGTTACAGGATTCGAAA
AACCCGCATACTAACACTTGCAAAGTTACAACACCCCATACTCCCTAATTTAATTAG
TTTTAATCTCAGCATACCATGCAACTATACACGTATCTTCTGTGCTTACACGTGTCCCA
TTCTCCAACCGACCAAGACACACTACAAATGTCCCGATGGTTTGGAGAGACAAAACA
GAGTTTCTACACAGCAACAATCACTTTGAGAAAAAGCTTTAATTGTCGTTTCATATTTT
ACACATTTGAAGGAAAAGAAAA-3' → ORF

SEQ ID NO: 3

Fig. 11

SEQUENCE LISTING

```
<160> NUMBER OF SEQ ID NOS: 37

<210> SEQ ID NO 1
<211> LENGTH: 3380
<212> TYPE: DNA
<213> ORGANISM: Brassica napus

<400> SEQUENCE: 1
gtcatggaat tctttgttag attaaaatat aaatcttaaa taaattgtcc ataaattcgt      60
ataaaatata ttttcacatg tttttttta aaactaggaa gagtttggat cttgagccct     120
agtctagctc cagagttggg attttcacta cttttgttaa gagttcttct taagtatgaa     180
tatacccatg tgtcatattc ttcatttgtt ctcatgttta tgtttcagtt catattcttc     240
atttgtacca atccaggtga agtagaagat attatatttg ttcgattctc tagcttgttt     300
aaatttacta gccggctact ggtgctggtt tgtgtttgat acatggttga aggactcatc     360
tcttttttac cgttatcgta tatatcataa gtagtggcgt caactcgaat gttaccaacg     420
tttggtaatt tttcgtttgc ggcgcgtcta tttctcacgt acctgataga gtatttatat     480
aatttataga aaagcattgt atccccattc gattaaacat ggtaagtatt ttcattggct     540
agttgtcaca cgtataacaa ggctaattaa ttatatgtgg atgtgaatac atagttcaaa     600
ctaaacctcg aagtagatga gatcaattca attcaaaaaa ctttagtaag acggagaccg     660
ggacttctct ctctcctctg tgagatgagt gttgaagctt ttcgcccggt gctctatctt     720
tgcttttgat tcttgttttc ttgggctttg aatccgggaa gccgtttgct ctttagttct     780
tacgcaggct tcgctagttc tgtttccggg agaaggaggc ttccttggct ccgtttctcg     840
ccggcttacg attccgaggt gtggaggctc cgagcctagc gccgttggct ttgattatca     900
cccctttcct caagggtgtg acttcagctt tgctcgtgat ttatgtgctc ttggtttagt     960
```

```
tccctctgaa gagatctcga atagatcgaa tgtttctctt cgatggtgtt gacatcaaac    1020
aagaggaggt gtgggattac tttaatcccg tgattggcgg cttggtggct caggatgagc    1080
tctcgaagtg gttcgatgga agctctccgg agaagagctc agccgtggat ggtggtcgcg    1140
atgtcgggta tggtttccgg tgatgagttg catgttccct ccggcgatgg aggcaggaga    1200
aggggtttgg cgacacgtgt gcctcgcagt tgaggtctca acacgtgggc cgttgtgctg    1260
tcgtttggga cggtggcatc ttttttgggc tttgttgggc cgggattttta gacgctcctt    1320 ttgttggttt ttttttttagg ttttaggtcc atcttggtct ttcgctgtaa tggttgtatg    1380
gggtttggtt ctgttggact cttttttataa taataataat aatagatgga aaaaaaaaa    1440 aaaaaaaaaa cctcgaagtt gtctggatac ttctatatttt taagtttcga tttcagcgaa    1500
ctggtgacca agtgatgttt gattatttga caatgtcacg gaaacatgca tgtaacaacc    1560
gatacaaatg gtcaaaactt aacatagcca tattgatatt ataacatgcg gcgccacact    1620
tatggtgttg acacgtagca agcatcttca gttaaccata acgtgtcgca accacacagg    1680
ataacacgta caagatcgag aaaccgcata ctaaacactg gcaaactaca acacccatac    1740
tcactaattt aattagcttt taatctcaac acaccacgca gctatacacg tgtcttctat    1800
gccaacacgt gccttgttct caaaccgacc aagacacact ataaatgtct cgatggtttg    1860
gagagacaat acacattttc tacacagcaa caaacacttt aagaaaaagc tttaattgtc    1920
gtttcatatt tgctcatttg aagaaaagaa aaatggcgtc taaccaacag agctacaaag    1980
ctggtgaaac cagaggcaag actcaggtac taataatata atacgtctac atatctatat    2040
atgtatctta ttctctttttc aagttctaaa gatgatttgg ttgtgtaata acaggagaag    2100
acaggacaag ctatgggagc gatgagggac aaggctgagg aaggcaggga caagacttcc    2160
caaacggccc aaacagccca acaaaggct caggagacgg cccaggcagc gaaagacaag    2220
acatctcaag ctgcccaaac gacgcagcaa aaggcgcatg aaacaacaca ggcaacaaaa    2280
gacaagacct ctcaagctgc ccaaacgacc cagcaaaagg ctcatgagac gacccaagca    2340
gcaaaagaca agacatctca agctgctaag acggcccaag aaaaggccca tgagacgaag    2400
gacaaaaccg gaagttacat gtccgagaca ggagaagcca taaagcagaa ggctcaaaac    2460
gctgctcagt acacaaagga gacggctcaa gaagcggctc agtacacgaa agagacggct    2520
gaagccggta gagacaagac cggtgggttc ttgagccaga caggtgagca agtgaagcag    2580
atggcgatgg gtgcagctga tgcggtgaaa cacacttttg ggatggctac ggaggaagaa    2640
gacaaggaac attatccagg cacaactacg accactactg gtactactcg gaccactgat    2700
cctactcatc atacttatca gaaggaagtg atgatagcaa gagaattatg taacgtgtct    2760
tttcttttgt ttctatattg tcttgtttgg tcttttgact tttcagtgtc tttgtttgtt    2820
atctctgtcg tgtccttgtg tttgtgattc cctcatgcat cttttgttgt gacggtgatc    2880
ctggagactt ctaatttcca gccaataagt ttagatttga tcccattgca acttttgtat    2940
cgtccaattt gtattcttgt tttaaataaa cagttattaa ttccatacca ttatccactt    3000
tatctaatgg actaggtgat aacccgcgcc ttgcgcggaa taaaattatt aattttaata    3060
tttataagat aagaagatat taaatctgtt tagtgtggac atcgatttgg ttttaggttg    3120
gattttttta gatttaactc ttttaaaata taacaactat tcggaagctg tatttatttt    3180 ggttgttcg attaaactga ttttcatttt tctttcttttc ggtgatagat tgcagttgga    3240
atatatatcg attattgcaa actttatgtt aaaaaacttg atatcttacc tgatacaatc    3300
```

```
agttagattt aatgcgatca tccttccatt ttttaaataa atatataata aatatcctta    3360
agccaattaa gtaaattgaa                                                3380

<210> SEQ ID NO 2
<211> LENGTH: 1952
<212> TYPE: DNA
<213> ORGANISM: Brassica napus

<400> SEQUENCE: 2
gtcatggaat tctttgttag attaaaatat aaatcttaaa taaattgtcc ataaattcgt      60
ataaaatata ttttcacatg tttttttta aaactaggaa gagtttggat cttgagccct     120
agtctagctc cagagttggg atttcacta cttttgttaa gagttcttct taagtatgaa      180
tatacccatg tgtcatattc ttcatttgtt ctcatgttta tgtttcagtt catattcttc     240
atttgtacca atccaggtga agtagaagat attatatttg ttcgattctc tagcttgttt     300
aaatttacta gccggctact ggtgctggtt tgtgtttgat acatggttga aggactcatc     360
tcttttttac cgttatcgta tatatcataa gtagtggcgt caactcgaat gttaccaacg     420
tttggtaatt tttcgtttgc ggcgcgtcta tttctcacgt acctgataga gtatttatat     480
aatttataga aaagcattgt atccccattc gattaaacat ggtaagtatt ttcattggct     540
agttgtcaca cgtataacaa ggctaattaa ttatatgtgg atgtgaatac atagttcaaa     600
ctaaacctcg aagtagatga gatcaattca attcaaaaaa ctttagtaag acggagaccg     660
ggacttctct ctctcctctg tgagatgagt gttgaagctt ttcgcccggt gctctatctt     720
tgcttttgat tcttgttttc ttgggctttg aatccgggaa gccgtttgct ctttagttct     780
tacgcaggct tcgctagttc tgtttccggg agaaggaggc ttccttggct ccgtttctcg     840
ccggcttacg attccgaggt gtggaggctc cgagcctagc gccgttggct ttgattatca     900 ccccttttcct caagggtgtg acttcagctt tgctcgtgat ttatgtgctc ttggtttagt     960
tccctctgaa gagatctcga atagatcgaa tgtttctctt cgatggtgtt gacatcaaac    1020
aagaggaggt gtgggattac tttaatcccg tgattggcgg cttggtggct caggatgagc    1080
tctcgaagtg gttcgatgga agctctccgg agaagagctc agccgtggat ggtggtcgcg    1140
atgtcgggta tggtttccgg tgatgagttg catgttccct ccggcgatgg aggcaggaga    1200
aggggtttgg cgacacgtgt gcctcgcagt tgaggtctca acacgtgggc cgttgtgctg    1260
tcgtttggga cggtggcatc ttttttgggc tttgttgggc cgggatttta gacgctcctt    1320
ttgttggttt ttttttttagg ttttaggtcc atcttggtct ttcgctgtaa tggttgtatg    1380
gggtttggtt ctgttggact cttttttataa taataataat aatagatgga aaaaaaaaa    1440 aaaaaaaaaa cctcgaagtt gtctggatac ttctataattt taagtttcga tttcagcgaa    1500
ctggtgacca agtgatgttt gattatttga caatgtcacg gaaacatgca tgtaacaacc    1560
gatacaaatg gtcaaaactt aacatagcca tattgatatt ataacatgcg gcgccacact    1620
tatggtgttg acacgtagca agcatcttca gttaaccata acgtgtcgca accacacagg    1680
ataacacgta caagatcgag aaaccgcata ctaaacactg gcaaactaca acacccatac    1740
tcactaattt aattagcttt taatctcaac acaccacgca gctatacacg tgtcttctat    1800
gccaacacgt gccttgttct caaaccgacc aagcacacact ataaatgtct cgatggtttg    1860
gagagacaat acacattttc tacacagcaa caaacactttt aagaaaaagc tttaattgtc    1920
gtttcatatt tgctcatttg aagaaaagaa aa                                  1952
```

<210> SEQ ID NO 3
<211> LENGTH: 1661
<212> TYPE: DNA
<213> ORGANISM: Brassica napus

<400> SEQUENCE: 3

```
tttccaatat ggattttgga aaaaccgggg aaaatgttat taaccatttt aaccaaaaat      60
atatgggcta acatatggg gaattaaact taaccggaat gtaagtgggg atgcctcaac      120
tatggtcgtt tatgggacaa tataacccctt ggagaacata ttatttattt gtttcatggt     180
cacgtttcaa ttcgatcatg ttttgcatgg actattatta gtactcgtca cagtaaaagc      240
tgaagatatg gtatagaaca gtagaacccc aaaagaaatc gtatagatca aactgttact      300
ttctgtaaaa aaaaatccgt taaaaaaatg attttgcatt tcagaatcac taaaaagaaa      360
tcttaaatct aatttagata aacggtaaat tgtgtggttt ataaggaata tcagcaatga      420
taaaaagtga aaacaatacg gaatttctca attgttgtgt attttattga tttaatatat     480
atatatatat atatatataa ttttttttttt tttttgaact ataaaaccat cgattatgag      540
acaaatattg taatttgagt ttcgcacaaa taaaagagta ctcctcttag ttttttctctt      600
atatattta ttattttcat ctacttatag attatgcaaa tgattctcaa tgataatgct        660
ataaaatggt tgtagataaa ggataaataa gggaggaaga atctggagta tataaaatag       720
ggaaaaatat ataaaactta ctgcctattg gtaaacattt tgagaaatat gggatcatta      780
aagttaaagt taagctgcaa ctgtggattc tgahtcatat gcagactgtg attgatacgt      840
tgttgaagta actcaccttt tgttttttttt tctctgttat atatagtatc atatgtattg     900
ctgccattca aaatttacta aattgttgtt aatttctat atcatcgtca tctggcgcca        960
ttcgaatttt actacatata tgttgttcta acatttgtgc taatattttc aacgtgcatc      1020
agtctgggtt gtatttcatt ggctagttgt cacacatcga acaaggctaa tcatatgtgg      1080
aggtgagtac gtagttcaag gactaacctc gaagttgctc gttttcggga atactttat      1140
attatcaatt ttgatttcaa aacgctaaag agtattttaa tgtactatct ctaagtgatg      1200
tttgattgtt tgacacggtt acggaacatg cacgtaacga ccgatacaca atgaagaaca      1260
aaaattatga taagccatat tgatagtaat atattataac atgcggtgaa cgacacttct      1320
tgtgtcacca cgttatcaag catcctttca atcaaccatg atgttgttcg caaccacaga      1380
agaacaacac gttacaggat tcgaaaaacc cgcatactaa cacttgcaaa gttacaacac      1440
ccccatactc cctaatttaa ttagtttaa tctcagcata ccatgcaact atacacgtat       1500
cttctgtgct tacacgtgtc ccattctcca accgaccaag acacactaca aatgtcccga      1560
tggtttggag agacaaaaca gagtttctac acagcaacaa tcactttgag aaaaagcttt      1620
aattgtcgtt tcatatttta cacatttgaa ggaaaagaaa a                         1661
```

<210> SEQ ID NO 4
<211> LENGTH: 18
<212> TYPE: PRT
<213> ORGANISM: Brassica napus

<400> SEQUENCE: 4

Met Ala Ser Asn Gln Gln Ser Tyr Lys Ala Gly Glu Thr Arg Gly Lys
1               5                   10                  15

Thr Gln

<210> SEQ ID NO 5
<211> LENGTH: 18

```
<212> TYPE: PRT
<213> ORGANISM: Brassica napus

<400> SEQUENCE: 5

Met Ala Ser Asn Gln Gln Ser Tyr Lys Ala Gly Glu Thr Arg Gly Lys
1               5                   10                  15

Thr Gln

<210> SEQ ID NO 6
<211> LENGTH: 18
<212> TYPE: PRT
<213> ORGANISM: Brassica napus

<400> SEQUENCE: 6

Met Ala Ser Asn Gln Gln Ser Tyr Lys Ala Gly Glu Thr Arg Gly Lys
1               5                   10                  15

Thr Gln

<210> SEQ ID NO 7
<211> LENGTH: 18
<212> TYPE: PRT
<213> ORGANISM: Brassica napus

<400> SEQUENCE: 7

Met Ala Ser Asn Gln Gln Ser Tyr Lys Ala Gly Glu Thr Arg Gly Lys
1               5                   10                  15

Thr Gln

<210> SEQ ID NO 8
<211> LENGTH: 18
<212> TYPE: PRT
<213> ORGANISM: Arabidopsis thaliana

<400> SEQUENCE: 8

Met Ala Ser Asn Gln Gln Ser Tyr Lys Ala Gly Glu Thr Arg Gly Lys
1               5                   10                  15

Ala Gln

<210> SEQ ID NO 9
<211> LENGTH: 19
<212> TYPE: PRT
<213> ORGANISM: Arabidopsis thaliana

<400> SEQUENCE: 9

Met Ala Ser His Gln Glu Gln Ser Tyr Lys Ala Gly Glu Thr Arg Gly
1               5                   10                  15

Lys Ala Gln

<210> SEQ ID NO 10
<211> LENGTH: 19
<212> TYPE: PRT
<213> ORGANISM: Daucus carota

<400> SEQUENCE: 10

Met Ala Ser His Gln Asp Gln Ser Tyr Lys Ala Gly Glu Pro Lys Gly
1               5                   10                  15

His Ala Gln

<210> SEQ ID NO 11
<211> LENGTH: 20
<212> TYPE: PRT
```

<213> ORGANISM: Hordeum vulgare

<400> SEQUENCE: 11

Met Ala Ser Asn Gln Asn Gln Gly Ser Tyr His Ala Gly Glu Thr Lys
1               5                   10                  15

Ala Arg Thr Glu
            20

<210> SEQ ID NO 12
<211> LENGTH: 20
<212> TYPE: PRT
<213> ORGANISM: Triticum aestivum

<400> SEQUENCE: 12

Met Ala Ser Asn Gln Asn Gln Ala Ser Tyr His Ala Gly Glu Thr Lys
1               5                   10                  15

Ala Arg Asn Glu
            20

<210> SEQ ID NO 13
<211> LENGTH: 20
<212> TYPE: PRT
<213> ORGANISM: Triticum aestivum

<400> SEQUENCE: 13

Met Ala Ser Asn Gln Asn Gln Ala Ser Tyr Ala Ala Gly Glu Thr Lys
1               5                   10                  15

Ala Arg Thr Glu
            20

<210> SEQ ID NO 14
<211> LENGTH: 18
<212> TYPE: PRT
<213> ORGANISM: Cicer arietinum

<400> SEQUENCE: 14

Met Ala Ser His Asp Gln Ser Tyr Lys Ala Gly Glu Thr Met Gly Arg
1               5                   10                  15

Thr Glu

<210> SEQ ID NO 15
<211> LENGTH: 18
<212> TYPE: PRT
<213> ORGANISM: Glycine max

<400> SEQUENCE: 15

Met Ala Ser His Arg Gln Ser Tyr Glu Ala Gly Gln Thr Lys Gly Arg
1               5                   10                  15

Thr Glu

<210> SEQ ID NO 16
<211> LENGTH: 20
<212> TYPE: PRT
<213> ORGANISM: Oryza sativa

<400> SEQUENCE: 16

Met Ala Ser His Gln Asp Gln Ala Ser Tyr Arg Ala Gly Glu Thr Lys
1               5                   10                  15

Ala His Thr Glu
            20

```
<210> SEQ ID NO 17
<211> LENGTH: 20
<212> TYPE: PRT
<213> ORGANISM: Oryza sativa

<400> SEQUENCE: 17

Met Ala Ser Gln Gln Glu Arg Ala Ser Tyr His Ala Gly Glu Thr Lys
1               5                   10                  15

Ala Arg Ala Glu
            20

<210> SEQ ID NO 18
<211> LENGTH: 18
<212> TYPE: PRT
<213> ORGANISM: Gossypium hirsutum

<400> SEQUENCE: 18

Met Ala Ser His Glu Gln Ser Tyr Lys Ala Gly Arg Ala Glu Gly Arg
1               5                   10                  15

Ala His

<210> SEQ ID NO 19
<211> LENGTH: 20
<212> TYPE: PRT
<213> ORGANISM: Zea mays

<400> SEQUENCE: 19

Met Ala Ser His Gln Asp Lys Ala Ser Tyr Gln Ala Gly Glu Thr Lys
1               5                   10                  15

Ala Arg Thr Glu
            20

<210> SEQ ID NO 20
<211> LENGTH: 21
<212> TYPE: DNA
<213> ORGANISM: Artificial
<220> FEATURE:
<223> OTHER INFORMATION: Primer

<400> SEQUENCE: 20
ggtgggaaag cgcgttacaa g                                      21

<210> SEQ ID NO 21
<211> LENGTH: 21
<212> TYPE: DNA
<213> ORGANISM: Artificial
<220> FEATURE:
<223> OTHER INFORMATION: Primer

<400> SEQUENCE: 21
gtttacgcgt tgcttccgcc a                                      21

<210> SEQ ID NO 22
<211> LENGTH: 33
<212> TYPE: DNA
<213> ORGANISM: Artificial
<220> FEATURE:
<223> OTHER INFORMATION: Primer

<400> SEQUENCE: 22
ttttgaattc ctaaccaaca aagctacaaa gct                         33

<210> SEQ ID NO 23
<211> LENGTH: 33
```

```
<212> TYPE: DNA
<213> ORGANISM: Artificial
<220> FEATURE:
<223> OTHER INFORMATION: Primer

<400> SEQUENCE: 23
ttttggatcc atcacaaaca caaggacaca aca                    33

<210> SEQ ID NO 24
<211> LENGTH: 27
<212> TYPE: DNA
<213> ORGANISM: Artificial
<220> FEATURE:
<223> OTHER INFORMATION: Primer

<400> SEQUENCE: 24
ggaattcgca gcttgagagg tcttgtc                           27

<210> SEQ ID NO 25
<211> LENGTH: 19
<212> TYPE: DNA
<213> ORGANISM: Artificial
<220> FEATURE:
<223> OTHER INFORMATION: Primer

<400> SEQUENCE: 25
ttgatacatg gttgaagga                                    19

<210> SEQ ID NO 26
<211> LENGTH: 16
<212> TYPE: DNA
<213> ORGANISM: Artificial
<220> FEATURE:
<223> OTHER INFORMATION: Primer

<400> SEQUENCE: 26
tttcttttct tcaaat                                       16

<210> SEQ ID NO 27
<211> LENGTH: 21
<212> TYPE: DNA
<213> ORGANISM: Artificial
<220> FEATURE:
<223> OTHER INFORMATION: Primer

<400> SEQUENCE: 27
ttccggtgat gagttgcatg t                                 21

<210> SEQ ID NO 28
<211> LENGTH: 16
<212> TYPE: DNA
<213> ORGANISM: Artificial
<220> FEATURE:
<223> OTHER INFORMATION: Primer

<400> SEQUENCE: 28
tttcttttct tcaaat                                       16

<210> SEQ ID NO 29
<211> LENGTH: 21
<212> TYPE: DNA
<213> ORGANISM: Artificial
<220> FEATURE:
<223> OTHER INFORMATION: Primer

<400> SEQUENCE: 29
```

-continued

```
ttcgctgtaa tggttgtatg g                                    21

<210> SEQ ID NO 30
<211> LENGTH: 16
<212> TYPE: DNA
<213> ORGANISM: Artificial
<220> FEATURE:
<223> OTHER INFORMATION: Primer

<400> SEQUENCE: 30
tttcttttct tcaaat                                          16

<210> SEQ ID NO 31
<211> LENGTH: 21
<212> TYPE: DNA
<213> ORGANISM: Artificial
<220> FEATURE:
<223> OTHER INFORMATION: Primer

<400> SEQUENCE: 31
atattataac atgcggcgcc a                                    21

<210> SEQ ID NO 32
<211> LENGTH: 16
<212> TYPE: DNA
<213> ORGANISM: Artificial
<220> FEATURE:
<223> OTHER INFORMATION: Primer

<400> SEQUENCE: 32
tttcttttct tcaaat                                          16

<210> SEQ ID NO 33
<211> LENGTH: 21
<212> TYPE: DNA
<213> ORGANISM: Artificial
<220> FEATURE:
<223> OTHER INFORMATION: Primer

<400> SEQUENCE: 33
ttaatctcaa cacaccacgc a                                    21

<210> SEQ ID NO 34
<211> LENGTH: 16
<212> TYPE: DNA
<213> ORGANISM: Artificial
<220> FEATURE:
<223> OTHER INFORMATION: Primer

<400> SEQUENCE: 34
tttcttttct tcaaat                                          16

<210> SEQ ID NO 35
<211> LENGTH: 18
<212> TYPE: DNA
<213> ORGANISM: Artificial
<220> FEATURE:
<223> OTHER INFORMATION: Primer

<400> SEQUENCE: 35
tttcttttcc ttcaaatg                                        18
```

```
<210> SEQ ID NO 36
<211> LENGTH: 19
<212> TYPE: DNA
<213> ORGANISM: Artificial
<220> FEATURE:
<223> OTHER INFORMATION: Primer

<400> SEQUENCE: 36
ataaggaata tcagcaatg                                                19

<210> SEQ ID NO 37
<211> LENGTH: 268
<212> TYPE: PRT
<213> ORGANISM: Brassica napus

<400> SEQUENCE: 37

Met Ala Ser Asn Gln Gln Ser Tyr Lys Ala Gly Glu Thr Arg Gly Lys
1               5                   10                  15

Thr Gln Glu Lys Thr Gly Gln Ala Met Gly Ala Met Arg Asp Lys Ala
            20                  25                  30

Glu Glu Gly Arg Asp Lys Thr Ser Gln Thr Ala Gln Thr Ala Gln Gln
        35                  40                  45

Lys Ala Gln Glu Thr Ala Gln Ala Ala Lys Asp Lys Thr Ser Gln Thr
50                  55                  60

Ala Gln Thr Thr Gln Gln Lys Ala His Glu Thr Thr Gln Ala Thr Lys
65                  70                  75                  80

Asp Lys Thr Ser Gln Ala Ala Gln Thr Thr Gln Gln Lys Ala His Glu
                85                  90                  95

Thr Thr Gln Ala Ala Lys Asp Lys Thr Ser Gln Ala Ala Lys Thr Ala
            100                 105                 110

Gln Glu Lys Ala His Glu Thr Lys Asp Lys Thr Gly Ser Tyr Met Ser
        115                 120                 125

Glu Thr Gly Glu Ala Ile Lys Gln Lys Ala Gln Asn Ala Ala Gln Tyr
130                 135                 140

Thr Lys Glu Thr Ala Gln Ala Ala Gln Tyr Thr Lys Glu Thr Ala
145                 150                 155                 160

Glu Ala Gly Arg Asp Lys Thr Gly Gly Phe Leu Ser Gln Thr Gly Glu
                165                 170                 175

Gln Val Lys Gln Met Ala Met Gly Ala Ala Asp Ala Val Lys His Thr
            180                 185                 190

Phe Gly Met Ala Thr Glu Glu Glu Asp Lys Glu His Tyr Pro Gly Thr
        195                 200                 205

Thr Thr Thr Thr Thr Gly Thr Thr Arg Thr Thr Asp Pro Thr His His
        210                 215                 220

Thr Tyr Gln Lys Glu Val Met Ile Ala Arg Glu Leu Cys Asn Val Ser
225                 230                 235                 240

Phe Leu Leu Phe Leu Tyr Cys Leu Val Tyr Ser Phe Asp Phe Ser Val
                245                 250                 255

Ser Leu Phe Val Ile Ser Val Val Ser Leu Cys Leu
            260                 265
```

BNLEA3-1 PROMOTER

CROSS-REFERENCE TO RELATED APPLICATIONS

This application is a division of U.S. patent application Ser. No. 10/387,384 filed Mar. 14, 2003 now abandoned, which claims the benefit of U.S. Provisional Patent Application 60/364,115 filed Mar. 15, 2002.

FIELD OF THE INVENTION

The present invention relates to promoters for molecular farming and/or early detection of transgenic plants.

BACKGROUND OF THE INVENTION

Seed development occurs in three overlapping phases. Initially a developmental pattern for embryo body plan and supporting tissue is established and elaborated, followed by synthesis of nutrient reserves for future use in nursing a germinating embryo to its autotrophic state, and finally preparation for the existence of a seed as a dormant entity awaiting favourable conditions for its next life cycle (Thomas 1993; Bewley and Black 1994; Goldberg et al., 1994; Wobus and Weber, 1999). Even after an embryo has attained its ability to potentially grow into a plant, the so-called maturation phase continues and then culminates in metabolic quiescence. This preparative phase includes progressive desiccation to retain in fully mature seeds a water content of only 5-15% that is sufficient to maintain cellular integrity but not to sustain normal biochemical activity. This phenomenon contrasts so-called orthodox seeds (storable as dry seeds) from seeds that are recalcitrant to storage (Farnsworth, 2001). Recalcitrant seeds do not dehydrate during their development but instead proceed to germinate, and in fact do not survive if dehydration is imposed. Vivipary, a variation in which embryos germinate prior to dispersal from their parent, also lacks a dehydration phase. Some consider embryogenesis-to-germination as a primitive feature into which desiccation has been interposed subsequently. However, there is no clear-cut pattern and the ability to desiccate is possibly an acquisition that occurred at multiple times in various taxa (Pammenter and Berjak, 2000). The uncertainty of the evolutionary chronology of the phenomenon aside, the ability of a seed to desiccate—and the cellular events pertinent to it—can impact pre-harvest physiology and post-harvest characteristics such as seed storage and vitality.

During seed maturation phase, proteins unrelated to major storage reserves also accumulate and continue to do so long after the storage genes cease their transcription. Initially found in wheat, and referred to as early methionine-labelled protein gene (Em) (Grzelczak et al., 1982; Cuming, 1984), related late embryogenesis abundant (LEA) proteins were recognized formally as a new group of proteins in cotton seeds (Baker et al., 1988). These are also structurally related to some of the proteins identified independently as being associated with responses to abiotic stress factors such as cold, dehydration and salinity, and abscisic acid treatment in vegetative parts and seed tissue ((Dure et al., 1989; Mundy et al., 1990; Bray, 1994; Close et al., 1993; Thomas, 1993; Dure, 1997). Following the discovery of LEA proteins in other species, Dure et al (1989) employed predicted structural features of the LEA proteins to classify them into three typical groups, and later into at least five groups (Bray, 1994; Moons et al., 1997; Cuming, 1999). All the groups have some typical common features such as high overall hydrophilicity and general paucity of Cys and Trp residues (Dure, 1997). Characteristically, Most of these proteins do not coagulate on boiling and remain soluble hence the use of the term "boiling-stable" in the literature.

Various groups of LEA proteins are also synonymously referred to with a "D-numeral", for example Group 1 as D19 family, which signifies the relationship to the embryogenesis-associated cDNA clones of cotton seeds (Dure, 1997). Group 1 LEA proteins have a 20-aa segment that is repeated 2 to 4 times in some species. The Em protein of wheat is a classical member of this group (Grzelczak et al., 1982; Quatrano et al. 1997). The group members are rich in Gly, are highly hydrated, and have random coil conformation (McCubbin and Kay 1985). Group 2 LEA (D11 family), the largest class, includes proteins that have been referred to under various names such as dehydrins, COR and RAB, and shows a wide variation in polypeptide size (9 to 200 kDa) (Bray et al., 1994; Close, 1997; Thomashow, 1999). The biological contexts in which these proteins were identified are quite diverse: dehydrating leaves, ABA-treated vegetative tissue, desiccating embryo, cold- or salinity-stressed tissues. The Group 2 proteins have one to 11 copies of a Lys-rich 15-mer unit (K-domain), and additionally either a Y-domain near the N-terminus or a poly-Ser domain or both. These proteins are also largely amorphous. Group 3 LEA (D7) proteins are dealt with after Group 4 (D113). The latter contains structurally bipartite proteins that have a Lys- and Glu-rich helical region followed by a Gly-rich random coil of highly variable length among different members (Ingram and Barterls, 1996).

The common feature of Group 3 Lea proteins is the presence of a 11-aa repeat in the polypeptide (Dure et al., 1989). Members of this group include cotton D7 (Baker et al., 1988), barley HVA1 (Straub et al., 1994), carrot Dc3 (Seffens et al., 1990) and Dc8 (Dure, 1993a), and rapeseed LEA76 (Harada et al. 1989). The 11-mer is a motif in which all but Position 10 contain an aa of specific chemical characteristic. Positions 1, 2, 4, 5 and 9 have mostly Ala, Thr, and to a lesser extent Val, aa that have side chains terminating in methyl group, and Positions 3, 7 and 11 have polar aa Glu, Gln, or Asp, and Positions 6 and 8 have positively charge aa Lys or Arg (Dure, 1993). The 11-mer repeats are predicted to result in an amphipathic helices in which one face contains the methylated aa in hydrophobic stripe and the other contains polar and charged aa; potential ionic bridges, for example, between Lys of Position 8 and Glu of Position 11, are considered to stabilize the helix. The remarkable positional conservation of hydrophobic, polar and charged aa does indicates a functional constraint despite the taxonomic divergence of the species where these proteins occur.

All LEA proteins have a common physiological context. Their production is associated with intracellular desiccation caused by or associated with various developmental (seed maturation), hormonal (ABA) and environmental conditions (drought, salinity, cold). Although ABA is intimately associated with cellular dehydration, ABA-induced LEA gene expression in vegetative tissues varies from undetectable (Prieto-Dapena et al., 1999) to high (Straub et al., 1994).

Jasmonic acid (JA) is involved in various processes including wounding response, senescence, pathogen attack, fruit removal and under dehydration (Creelman and Mullet, 1995). JA also interacts with ABA in modulating ABA-inducible gene transcription (Hays et al., 1999). Recently, Swiatek et al (2002) reported that JA and ABA regulated cell division progression differentially.

Cellular dehydration is countered with accumulation of compatible solutes such as glycine betaine (Jain and Selvaraj, 1997; Nuccio et al., 1999) to a certain extent, but extensive loss of bulk water and especially bound water can lead to irreversible damages of oraganelles, membranes, proteins and enzymes. The concomitant increase of ion concentration would worsen the intracellular conditions. The coincidental high-level accumulation of LEAs under developmental and environmental dehydration, intracellular location, and the generally amorphous structure and the very high water-carrying capacity of LEAs have favored a non-enzymatic role for LEAs in safeguarding the cellular entities. These include hydration, water substitution in hydrogen bonding to membrane polar heads, and acquisition of a glassy state, and ion sequestration (Bartels et al., 1988; Lane 1991; Close et al., 1993; Ried and Walker-Simmons, 1993; Dure, 1997; Thomashow, 1999). Group 3 LEAs, because of their 11-aa modules of predicted helices, are considered to prevent salt precipitation and deleterious crystal formation by trapping ions (Dure, 1997). Interestingly, LEA3 proteins from pollen can stabilize glasses in vitro due to the possible formation of tight hydrogen bonding network with sugars (Wolkers et al., 2001). As evident from the foregoing, groups of unstructured proteins with lax primary and higher order organization cannot be collectively understood by paradigms since there is no paradigm per se for such proteins, but the examples do provide a starting point. The accumulation of Group 3 LEA proteins correlates with dehydration tolerance in wheat seedlings (Ried and Walker-Simmons, 1993) and cold acclimation efficiency in rice (Takahashi et al., 1994) and in *Chlorella* (Joh et al., 1995). Ectopic expression of the barley LEA3 (HVA1) in rice (Xu et al., 1996), tomato LE25 protein in yeast (Imai et al., 1996) result in enhanced drought and salt tolerance in transgenic rice, salt and freezing tolerance in yeast, respectively. *Brassica napus* (rapeseed; canola) is an economically important seed crop. The potential importance of LEA3 in seed development is not known. With the exception of an early report by Harada et al (1989) on LEA76 cDNA from a library of germinating seeds (14 hr after imbibition), there is very little information. The organization of LEA3 gene family or the promoter characteristics of its members have not been determined.

SUMMARY OF THE INVENTION

Here, we show that canola Lea3s (BnLEA3) belong to a small gene family, and we present a model proposing that the ancestor of these arose by exon shuffling. We further show that one of the BnLEA3 genes is highly seed-active, weakly inducible by ABA, and not responsive to abiotic stress factors, and that a version of its promoter is useful for molecular farming.

BRIEF DESCRIPTION OF THE DRAWINGS

FIG. 1. (A) Deduced amino acid sequence (SEQ ID NO: 37) of the coding region of the BnLea3-1 gene from *B. napus*. The 11-mer repeats are boxed. (B) Kyte-Doolittle hydrophilicity analysis with a 15-aa window that shows a large hydrophobic C-terminal end in BnLea3-1 and BnLea3-3.

FIG. 2. A comparison of coding region of Group 3 Lea genes from *B. napus*. Exon position/length, intron position and length and perfect 11-mer repeats and linker (L) repeats are indicated. The hydrophobic termini are marked in gray.

FIG. 6A. DNA sequence (SEQ ID NO: 1) and deduced amino acid sequence (SEQ ID NO: 37) of BnLea3-1 gene from isolated *Brassica napus*. The upstream promoter region is shown. Boxed is the putative TATA box. Bold and underlined are putative cis-elements responsible for seed-specific gene expression and a weak ABA-inducible expression in seedlings. The italicized region represents the primers used in the deletion studies.

FIG. 6B. Promoter region of BnLea3-1 (SEQ ID NO: 2). The putative TATA box is boxed and ABRE-like and other putative cis-acting elements are highlighted and underlined. The first transcription start site is indicated at position "+1". The primer sites designated for subsequent deletion analysis of the promoter are italicized and indicated by arrows.

FIG. 7. GUS staining in stable transgenic *B. napus* and tobacco seeds and in particle bombarded-pea seeds of indicated age in days after pollination (DAP) and in seeds of indicated days after imbibition (DAI). Transgenic line 9714-22 (*B. napus*) and 9714-15 (tobacco) were used here. GUS enzyme assay in developing seeds and leaf tissue in the above transgenic lines and in mature seeds of a transgenic line of each species with a GUS gene expressed under the control of a duplicated caMV35S promoter (n=3).

FIG. 11. Promoter sequence of BnLea3-2 (SEQ ID NO: 3).

Table 1. Homology comparison between first and second exon of Lea76 and other LEA3 proteins.

DETAILED DESCRIPTION

Currently there is substantial interest in altering seed development and metabolism. However, the widely used cauliflower mosaic virus 35S promoter from CaMV virus is not very active in seeds. Many abundantly expressed genes including seed storage proteins tend to be less active toward the later stages of seed development. Therefore, we decided to isolate seed-active promoters from *B. napus* and to functionally test them in *B. napus* and heterologous systems such as tobacco. In some plants such as cotton certain proteins known as LEA are accumulated during late seed development. We decided to isolate candidate genes by screening a genomic library of *B. napus*. The candidate genes could then be tested for expression and useful promoters could be characterized thereafter.

The regulatory sequences of candidate genes that are identified (as indicated above) would be furor characterized for their activity in *B. napus* and tobacco and pea. The promoter-GUS chimerical constructs would be introduced either transiently (bombardment) or through the *Agrobacterium*-mediated transformation technique. GUS activity would be measured histochemically or by fluorometric analysis. The isolation and functional testing of the promoter that is strongly active in the later stages of seed development and use of weak hormonal induction to predict its potential seed-borne activity very early at the seedling stage.

The BnLea3-1 promoter has been tested in stably transformed canola and tobacco seeds and in bombarded pea seeds. It is active in all three.

Figure 6A:
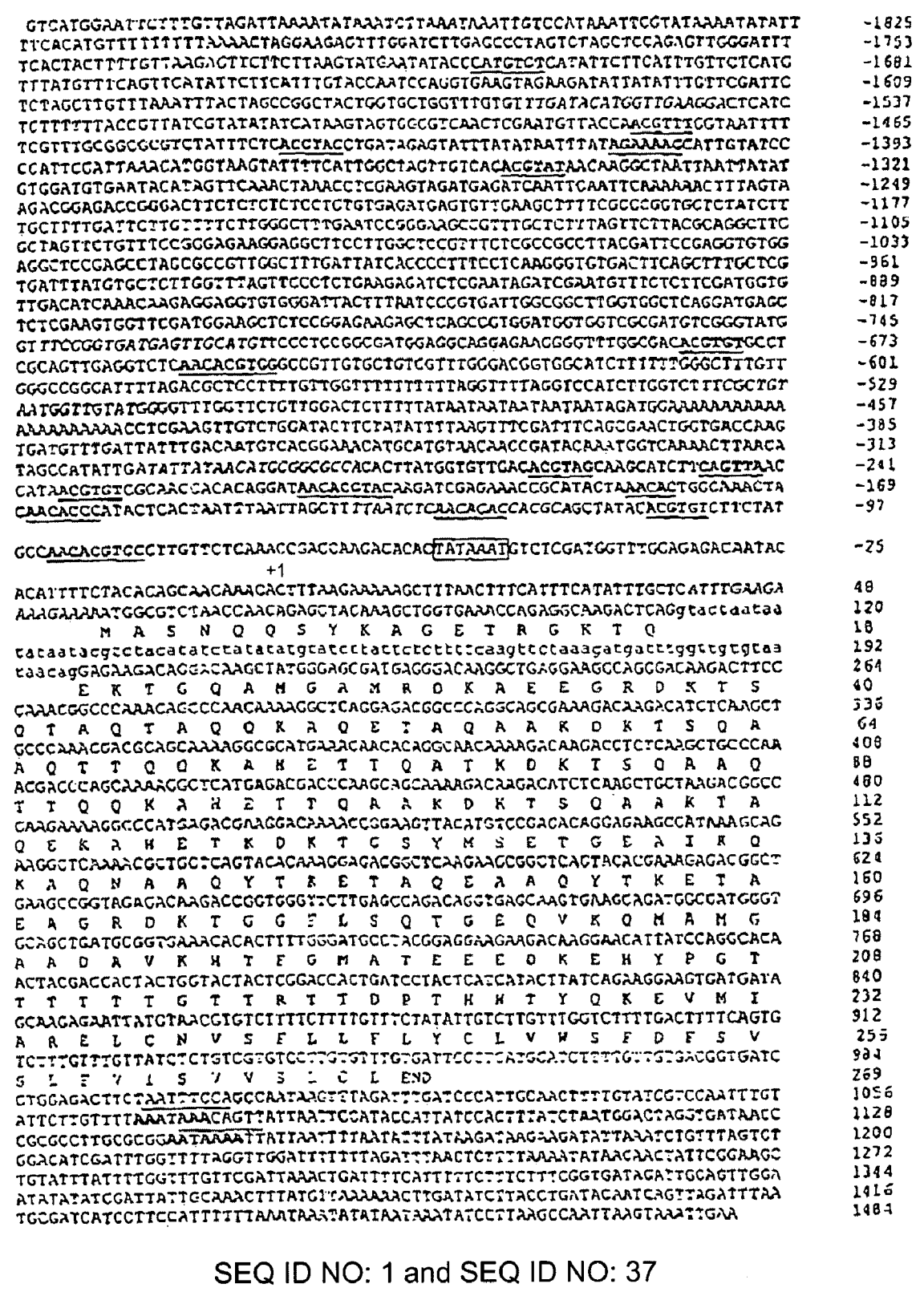

There are two seed active promoters that have been isolated from *Brassica Napus*. BnLea3-1 promoter (FIG. 6A and FIG. 6B) is most active in seeds from the time the seeds start to accumulate seed storage proteins to near maturity. Thus foreign proteins can be accumulated in mature seeds as shown by the example of GUS accumulation (FIG. 7).

The above promoter is not active in vegetative parts and it is not induced by environmental stress factors such as salinity, heat, cold, therefore the foreign protein will not be made elsewhere in the tissues tested. Thus, the protein would be confined to seeds.

The above promoter is, however, induced by ABA and methyl jasmonate (MeJA) in seedling tissue. Thus, among independent transgenic lines the ones that would express the protein most highly in the seeds due to favorable position effects may be identified very early in the life cycle of the transgenic by testing a small explant material following ABA/MeJA treatment. This would cut down the upstream operational cost of molecular farming.

Figure 8:
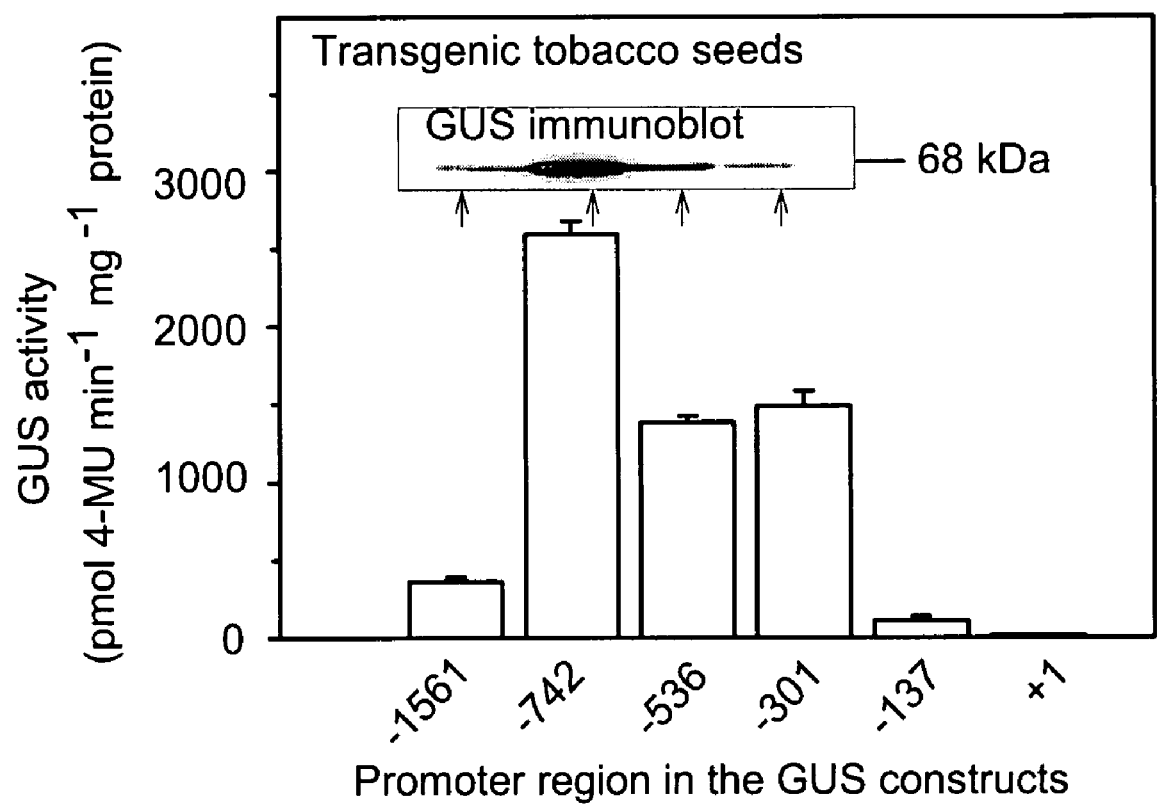
FIG. 8. Deletion analysis of BnLea3-1 promoter constructs with a GUS reporter in mature seeds of transgenic tobacco. GUS activity measured in triplicate samples. The segment of BnLEA3-1 promoter, in bp from the transcription start site (+1), is shown in the abscissa. The transgenic line numbers: −1561(9714-15); −742 (9727-16); −536 (9726-6); −301 (9724-7); −137 (9721-12); promoter-less (RD400).

A shortened version of the promoter (0.75 Kb) is approximately 5× more active than the long version (1.6 kb) and thus enhanced production of the foreign protein possible as demonstrated with GUS (FIG. 8).

In addition to BnLea3-1 promoter (SEQ ID NO: 2), another promoter that is not induced by ABA/MeJA or stress factor has also been isolated, and this promoter is also seed specific and thus useful in producing foreign proteins. The BnLea3-2 (SEQ ID NO: 3) is active in developing seeds from 20 DAP (days after pollination) to maturity. Structurally it is different from BnLea3-1 promoter regarding the cis-elements involved in ABA responsiveness. The BnLea3-2 promoter is 1.66 kb in length (FIG. 11). It is different from BnLea3-1 promoter, although a stretch near the proximal promoter region (1-400 bp) is very similar to that of BnLea3-1. Transgenic seed GUS activity driven by BnLea3-2 promoter is as strong as BnLea3-1.

The foreign proteins may be of intrinsic value as a "harvested material" or as a protein that modifies the seed composition and or form.

Plant Material, Stress and ABA Treatments

Both WT and transgenics of *Brassica napus* (cv. Westar; hereafter canola) and *Nicotiana tabacum* (cv. Xanthi; hereafter tobacco) were grown on Terra-lite Redi-earth (W. R. Grace & Co., Ajax, Ontario) in a controlled environment chamber set at 20° C. constant air temperature, and a 16-h day (220 µE $m^{-2}$ $s^{-1}$ PPFD) and 8-h night. A solution (0.33 g $L^-$) prepared from a commercial 20-20-20 fertilizer (Plant Products Co., Brampton, Ontario) was used to water the plants until harvesting. For stress and ABA treatments, two *B. napus* homozygous lines, 9714-22 (BnLea3-1::GUS) and 9715-22 (BnLea3-2::GUS) were used. Ten sterilized seeds from each line were germinated on 100 mL Murashige and Skoog (1962) basal medium (pH 6.5) solidified with 0.7% agar (w/v) in individual Majenta GA7 boxes (Chicago, Ill.). These were placed in an incubator set at 20° C. constant air temperature and 16 h day (50 µE $m^{-2}$ $s^{-1}$ PPFD) and 8-h night Germinated seedlings (7 d) were either kept in the same incubator (Control) or given various treatments for 2 d. Cold-treated plants were kept at 4° C. while heat-treated plants were grown in a heated growth cabinet (37° C.). Sterile stock solutions (20 mL) were added to the media to give final concentrations of following treatments: 150 mM NaCl, 150 mM mannitol, 10% PEG (MW 3350), 50 µM (±) ABA (in final 1% acetone, Sigmia), or 100 µM MeJA (in final 1% ethanol, Aldrich). Shoots and roots were harvested, powdered in liquid nitrogen and stored at −70° C. until needed. Seedlings (20 d) of 971422 (BnLea3-1:: GUS) and 9715-22 (BnLea3-2:: GUS) lines were subjected to various hormonal and stress treatments for 2 d before shoots and roots were harvested separately for protein extraction and subsequent fluorometric assay for GUS activity.

General Molecular Techniques and Analysis of Nuclear Acids

Polymerase chain reaction (PCR), agarose gel electrophoresis, isolation of plasmid DNA, restriction digestion and ligation of DNA, transformation of *E. coli* strains, DNA gel blot analyses, RNA gel blot analyses, were performed according to published procedures (Sambrook et al., 1989).

Genomic DNA was isolated from frozen young leaf tissues of canola and tobacco wild type (WT) plants and transgenics using the cetyl-trimethyl-ammonium bromide method (Rogers and Bendich, 1985). PCR-amplified BnLea3-3 DNA fragment (938 bp) was labeled with $^{32}$P-dCTP using rediprime™ II labeling system (Amersham Pharmacia Biotech) and added to the prehybridization solution consisting of 50% formamide, 5×SSC, 5× Denhardt's solution, 1% SDS, 10% dextran sodium sulfate (MW=400,000-600,000) and 100 μg mL$^{-1}$ sonicated salmon sperm DNA at 42° C. overnight. RNA was isolated with TRIzol (Life Technologies) according to the supplier's instructions and northern hybridization was performed as described previously (Huang et al., 2000). Membrane was washed under high stringency conditions at 65° C. with 0.1×SSC and 0.1% SDS. Two GUS gene-specific primers OL-2934 (5'-GGTGGGAAAGCGCGTTACMG-3') (SEQ ID NO: 20) and OL-2935 (5'-GTTTACGCGTTGCTTCCGCCA-3') (SEQ ID NO: 21) were used for RT-PCR reactions in this study.

Isolation of Group 3 LEA Genes from a Genomic Library

A library of *B. napus* cv. Westar in λ ZAP Express™ Vector was used in these screens. The sequence of pLEA76 (Harada et al., 1989) was the only sequence available for *B. napus* Group 3 LEAs. PCR primers based on these (OL-1204 TTTTGAATTCCTAACCAACAAAGCTACAAAGCT (SEQ ID NO: 22) and OL-1205 TTTTGGATCCATCACAAACACAAGGACACAACA (SEQ ID NO: 23)) were used to amplify the corresponding 938 bp genomic segment. This was cloned into pJH-1-11, the insert is referred to here as BnLEA3-3. Sequence analysis showed that it was LEA76 within the limits of the PCR amplicon, and it was subsequently used to identify three strongly hybridizing and two weakly hybridizing clones. The latter were pursued to be inclusive of all potential LEA clones, but were discounted later because of futile sequencing of the inserts. The remaining three clones, BnLEA3-1, 3-2 and 3-4 were characterized in this study.

DNA Sequencing and Sequence Analysis

DNA sequencing was done by the PBI DNA Technology Unit in an Applied Biosystems Model 373A DNA Sequencer with a Taq DyeDeoxy Terminator Cycle Sequencing Kit (Applied Biosystems). Overlapping sequence data from both strands for each clone were assembled and analyzed using DNAStar software (Madison, Wis.).

Transcription Start Site Determination

5'-RACE was used to determine the transcription start site of the BnLea3-1 promoter with the Marathon™ cDNA amplification kit (Clontech). The cDNAs were synthesized from total RNA isolated from 40 DAP Westar seeds using BnLea3-1 gene specific primer OL-2913 (5'-GGAATTCG- CAGCTTGAGAGGTCTTGTC-3' (SEQ ID NO: 24); EcoRI site underlined), amplified fragments were purified with the NucleoTrap purification kit (Clontech), and cloned into NotI and EcoRI sites of pBluescript II SK$^-$ (Strategene). The insert DNA in the plasmid was sequenced with OL-2913 and the 5' adapter primer provided by the supplier.

Construction of BnLea3-1, BnLea3-2, and BnLea3-4 Promoters and GUS Coding Region Fusion Vectors The full-length BnLea3-1 promoter and its 5'-truncated deletions, and promoter fragments from BnLea3-2 and BnLea3-4 were amplified from *B. napus* (Westar) genomic DNA by PCR using a mixture of Taq and Pfu (1:1) and sequence verified. After restriction digestion by SalI and BamHI, the PCR-amplified DNA fragments were inserted into the respective sites (Sal I at 5' and BamHI at 3') of a plant transformation vector pJH9713, a derivative from the vector pRD400 (Datla et al., 1992). The pJH9713 is obtained from the parental vector pRD400 by inserting a BamHI and EcoRI fragment containing the GUS-coding region and a Nos terminator excised from another vector pHS744. Although, pJH9713 was used as a transformation vector, someone skilled in the art will be able to practice the invention by cloning these promoters into another plant transformation vector and by transforming a plant species transiently or stably as described below by using BnLea3-1 promoter and promoter fragments as an example.

Oligos used to amplify BnLea3-1 promoter and its deletion fragments, as well as BnLea3-2 promoter are shown below:

```
A. BnLea3-1 Promoter and Fragments
-1561 bp 5'-TTGATACATGGTTGAAGGA-3'/5'-TTTCTTTTCTTAAAT-3'
         (SEQ ID NO: 25)            (SEQ ID NO: 26)

-742  bp 5'-TTCCGGTGATGAGTTGCATGT-3'/5'-TTTCTTTTCTTCAAAT-3'
         (SEQ ID NO: 27)             (SEQ ID NO: 28)

-536  bp 5'-TTCGCTGTAATGGTTGTATGG-3'/5'-TTTCTTTTTCTTCAAAT-3'
         (SEQ ID NO: 29)             (SEQ ID NO: 30)

-301  bp 5'-ATATTATAACATGCGGCGCCA-3'/5'-TTTCTTTTCTTCAAAT-3'
         (SEQ ID NO: 31)             (SEQ ID NO: 32)

-137  bp 5'-TTAATCTCAACACACCACGCA-3'/5'-TTTCTTTTCTTCAAAT-3'
         (SEQ ID NO: 33)             (SEQ ID NO: 34)

B. BnLea3-2 Promoter
-1200 bp 5'-TTTCTTTTCCTTCAAATG-3'/5'-ATAAGGAATATCAGCAATG-3'
         (SEQ ID NO: 35)           (SEQ ID NO: 36)
```

The PCR conditions used for amplifying the promoters and fragments are as follows: 95° C., 1 min, 1 cycle; 95° C., 1 min, 55° C., 1 min, 72° C., 1 min 30 seconds, 25 cycles; and 72° C., 10 min, 1 cycle.

Transient Assay of BnLea3-1 Promoter Activity

The vector harboring the BnLea3-1:: GUS fusion constrict was introduced into pea seeds (*Pisum sativum* cv Green Feast) after removing the seed coat and into leaf cells using a Bio-Rad helium driven biolistic particle delivery system (Model PDS 1000). The DNA for bombardment was prepared according to Nehra et al. (1994) using 1100 psi rupture disks (Bio-Rad). Bombarded materials were incubated in 0.89% agar-solidified Petri dishes at room temperature overnight, and stained for GUS activity (Jefferson, 1987).

Genetic Transformation of Plants

*Agrobacterium tumefaciens* GV3101 (pMP90) (Koncz and Schell, 1986) derivatives carrying the above transformation vectors were used for genetic transformation of *N. tabacum* (cv Xanthi) and *B. napus* (cv Westar) as described before (Nair et al., 2000). Primary transgenics were selected for kanamycin resistance, tested for GUS staining (Jefferson, 1987) where appropriate, tested by PCR for transgene and by Southern blot hybridization to verify the GUS integration into the genomes Homozygous lines were obtained for BnLea3-1:: GUS (9714 lines) by selfing.

Fluorometric β-glucuronidase (GUS) Assays and Histochemical Staining

Protein extraction and quantification for the fluorometric assay and histochemical staining of GUS activity essentially followed Jefferson (1987). The enzyme assays were replicated three times.

Protein Isolation and Immunoblotting

Five hundred mg of ground tissues were extracted with 0.5-ml extraction solution consisting of 50 mM sodium phosphate buffer, pH 7.0, 10 mM $Na_2EDTA$, 10 mM beta-mercaptoethanol, and 0.1% sodium lauryl sarcosine. Seed and leaf extracts containing 20 µg proteins were used in immunoblot analysis according to Nair et al (2000). GUS polyclonal antiserum (dilution 1/3500) raised in rabbits was used (Molecular Probes, Inc., Eugene, Oreg.).

There are Four LEA3 Genes in *Brassica napus*

Figure 3:
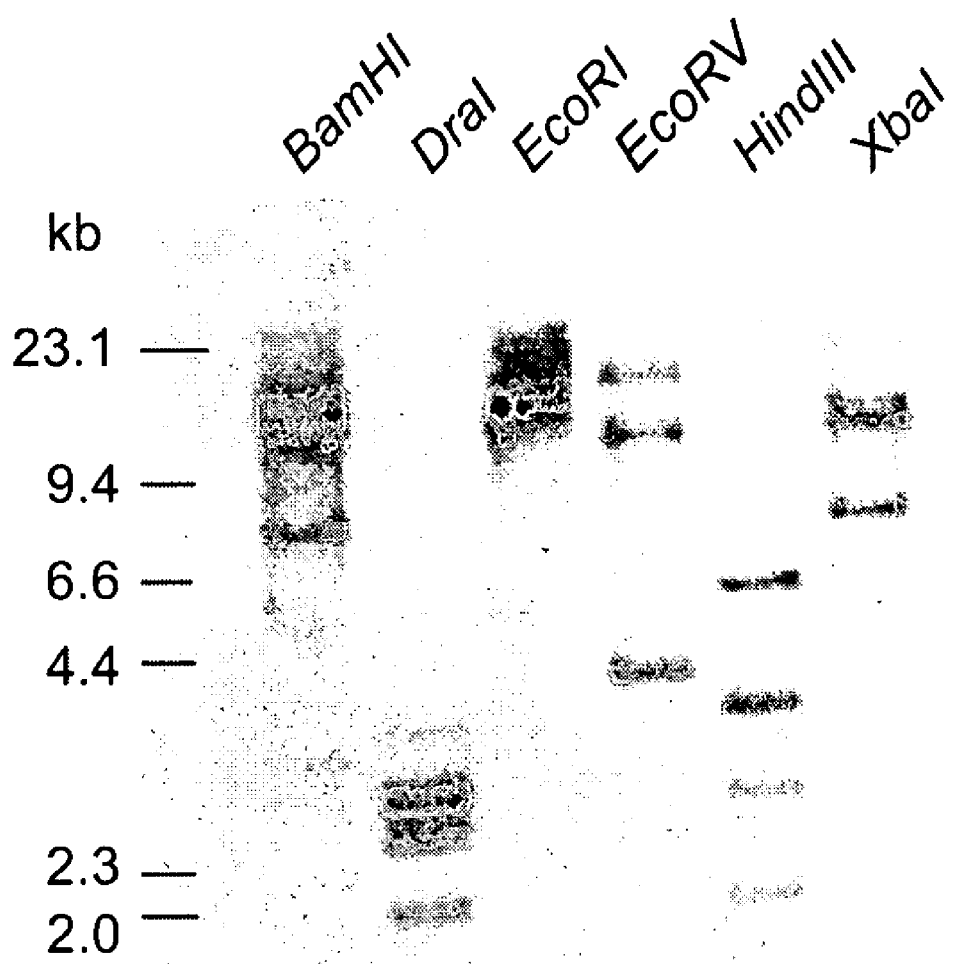
FIG. 3. Southern blot analysis of *B. napus* genomic DNA probed with a BnLea3-3 fragment (938 bp). The nucleotide sequence of this probe has been deposited in GenBank (accession number AJ535110). Twenty pg DNA from young leaves of *B. napus* was digested with BamHI, DraI, EcoRI, EcoRV, HindIII and XbaI, fractionated, blotted and hybridized as described in Materials and Methods.

A genomic library screen yielded three clones (BnLEA3-1, -2 and -4). These along with the genomic counterpart of LEA76 (BnLEA3-3; described in Methods), were sequenced. Initial analyses showed that all of them were similar but polymorphic enough to be regarded as representation of four independent genes of a family. The deduced aa sequence characteristics (aa) of BnLEA3-1 provide a framework for subsequent discussion of the familial characteristics. As shown in FIG. 1, the predicted gene product contains 268 aa, with eight 11-mer units followed by a 11-mer linker and three 11-mer units. The 11-mer units generally follow the hallmark pattern of Group 3 LEA proteins: Positions 1, 2, 4, 5, 9 contain mostly Ala or Thr; Gln, Glu or Asp at Positions 3, 7, and 11; and predominantly Lys or Arg at Position 6. The variations to this pattern, if any, are also identified in FIG. 1. The deduced open reading frames of the three other LEA3s from canola also contained the 11-mer units and the interposed linker (FIG. 2). The deduced polypeptides differed in their sizes: 161 aa in BnLEA3-2, 197 aa BnLEA3-4, and 280 aa in BnLEA3-3 (Accessions, AJ535109, AJ535111, AJ535110, respectively). BnLEA3-2 and BnLEA34 conformed to the general pattern of nearly end-to-end hydrophilicity of Group 3 LEAs (FIG. 1B). Notably, BnLEA3-l and BnLEA3-3 deviated from this pattern and contained a long hydrophobic stretch at their C-termini. The above analyses showed that all the four LEA3s were independent, and additional evidence will be discussed later. Southern blot analysis of *B. napus* cv Westar genomic DNA restricted with six different enzymes showed that the genome, despite being amphidiploid, contained only few bands hybridizing to BnLEA3-3 probe (FIG. 3). Thus, it seemed likely that the clones discussed above represented all LEA3 genes in canola, noting that the clones were identified from a genomic library and therefore were independent of any expression bias.

BnLEA3 Proteins are Organized According to an "18jX" Pattern

As shown in FIG. 2A, BnLEA3 gene products are encoded by two exons, and that the intron is in phase zero. In this pattern, Exon I encodes an 18-aa segment (18), the intron junction (j) does not disrupt a codon, and Exon II encodes a segment of variable length (X). We define this as "18jX" pattern. Accordingly, BnLEA3-l would be referred to specifically as 18j250 and generically as 18jX. As shown in FIG. 2A, the patterns of BnLEA3-2(18j143), BnLEA3-3 (18j262), BnLEA3-4 (18j 179) varied for the X portion and the larger ones were the ones to have a hydrophobic C terminus. In each of these cases, while the intron length varied, the Phase-zero position was retained. Considering that *B. napus* is an amiphidiploid (Truco et al., 1996), the above analyses suggest, but not prove, that BnLEA3-1 and BnLEA3-3 are counterparts and so are the two smaller, completely hydrophilic ones. Thus, one member of each set might have been derived from an ancestor of the diploid parents of the *B. napus*.

The 18jX Pattern is Bipartite with a Rigid "18" Portion (Exon I) and a Plastic X Portion (Exon II)

The 18jX pattern seemed to suggest that the larger, C-terminal hydrophobic ones were simple expansions of their shorter counterparts or the latter ones contractions of the former. If that were the case, the aa sequence of X in the four LEAs would be nearly identical except for the additional segment in BnLEA3-1 and BnLEA3-3. Amino acid sequence identity scores revealed an interesting trend (Table 1). The 18 portion was highly conserved (100%) among all the four LEAs, but the X portion varied substantially from 49 to 76% when the X of BnLEA3-1 was compared with that of the other three LEAs after trimming the right side overhang in the sequences. Even a liberal approach of gapped analysis did not improve the identity score substantially. Thus, it was clear that Exon I was held constant whereas, in relative terms, Exon II was highly variable. This pattern was consistent with the Exon Shuffling theory. Notable in this regard is the evidence for occurrence of 11-mer units in alga and animals. A model pertaining to these observations will be presented in Discussion.

Figure 4:
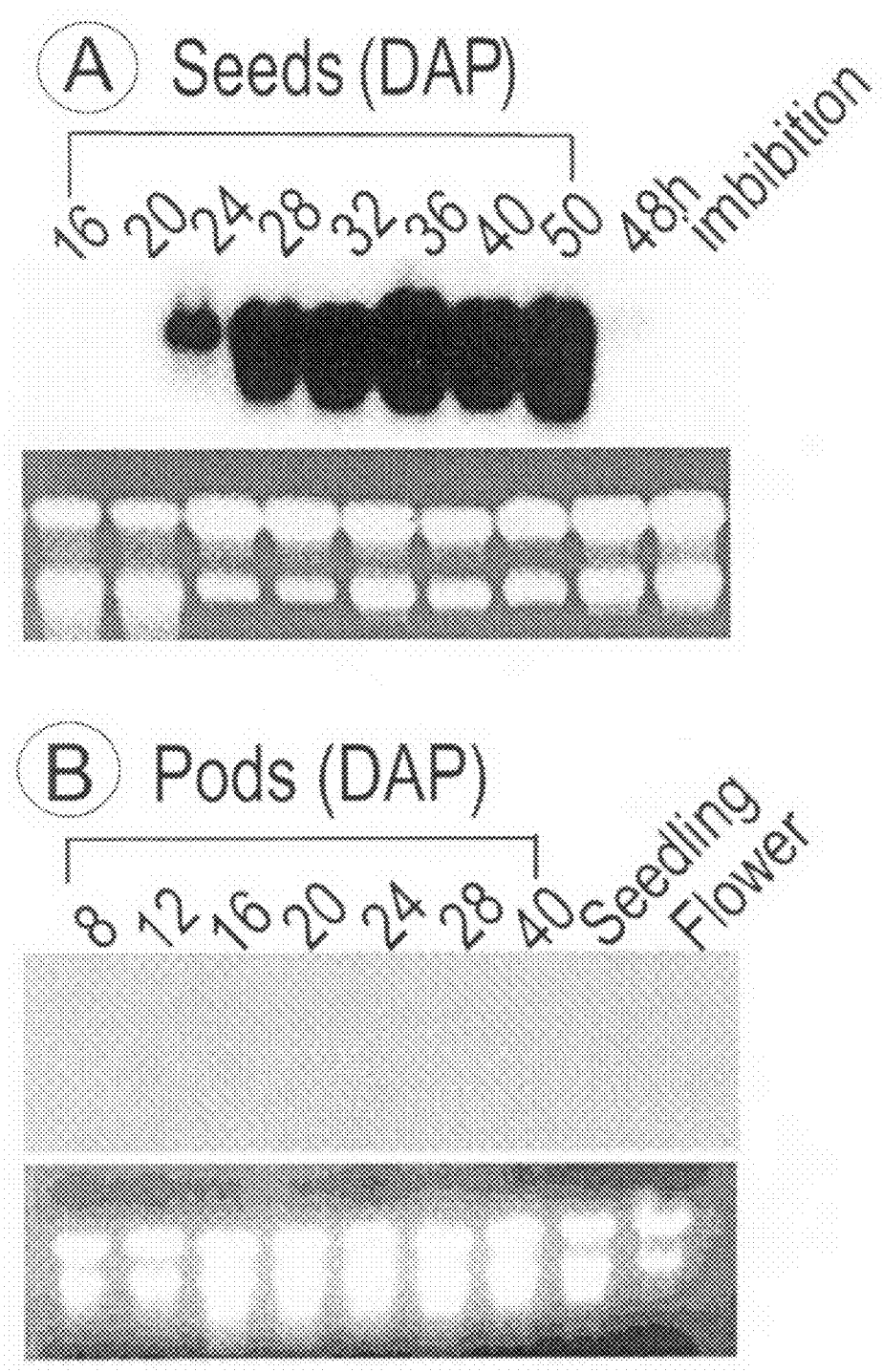
FIG. 4. Northern analysis of developing seeds (A) and non-seed tissues (B) for expression of BnLea3-1-like genes. Total RNA (15 µg) isolated from developing seeds, siliques without seeds, seedlings (7 d) or flowers (unopen) were fractionated, blotted and hybridized as described in Materials and Methods and FIG. 4.

BnLEA3 Gene Expression Spans the Phases of Storage Reserve Accumulation, Desiccation and Maturation in Seeds Northern analysis with BnLEA3-1 as a probe showed that BnLEA3-1-related transcripts accumulated in developing *B. napus* seeds from approximately 24 days after pollination (DAP) until maturity, and diminished in seed tissue collected 2 days after imbibition (DAT) (FIG. 4A). These transcripts were not detectable in empty siliques (seeds removed; shown as pods in FIG. 4B), seedlings or flower tissues. Although BnLEA3 gene family is a small one and the hybridizations were performed at high stringency, the possibility that the expression reported here is a sum for all the members of gene family was not ruled out.

Figure 5:
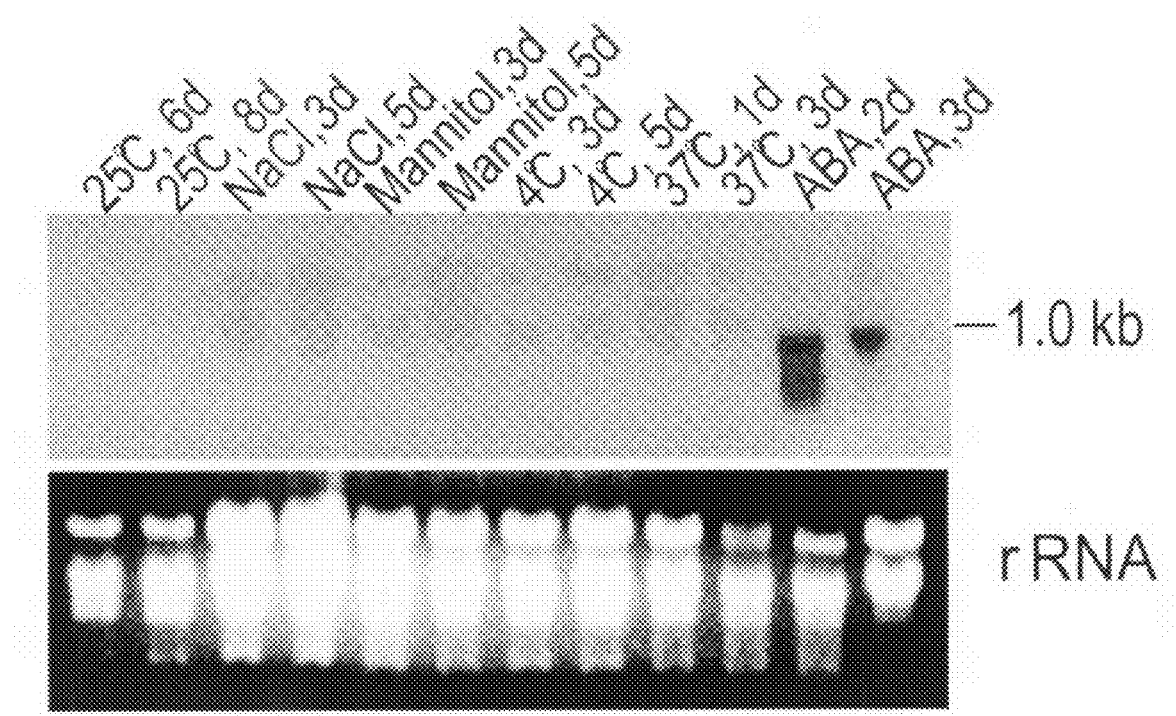
FIG. 5. Northern blot analysis of approximately 15 µg total RNA from *B. napus* aerial part of seedlings (7 d) exposed to abiotic stress conditions and 50 µM ABA for various periods of time (as indicated). Total RNA (15 µg) from the treated tissues were fractionated, blotted and hybridized with PCR-amplified BnLEA3-1 probe (see Detailed Description).

BnLEA3 Genes are not Responsive to Abiotic Stress Factors but are Induced by Abscisic Acid Treatment Transcriptional induction by abiotic stress factors is one of the features of LEA genes (Seffens et al., 1990; Shen and Ho, 1995; Delseny et al., 2001), but BnLEA3-1 or any of its closely related paralogs were found not to be induced. *B. napus* seedlings subjected to cold (4° C.), heat (37° C.), salinity (150 mM), or osmotic stress (150 mM mannitol) did not show any BnLEA3-1 transcript at all (FIG. 5). This indicated that in seedlings BnLEA3 genes were neither active nor inducible by the various abiotic stress conditions. However, treatment of the seedlings with ABA (50 µM) resulted in detectable steady-state levels of BnLEA3-1. These results might also suggest that none of the four LEA3 genes was active in vegetative tissue except when induced by ABA, if the observed hybridization was due also to other LEA3 genes BnLea3-1 Promoter Contains cis Elements Associated with Seed Expression and ABA Induction Since the promoter structure of any LEA3 genes from *B. napus* had not been characterized, the upstream region of the BnLEA3-1 coding region was sequenced and the putative cis elements (plus strand) present in seed storage proteins and ABA-inducible genes highlighted and underlined (FIG. 6B). The transcription start site (TSS) was determined using 5'-RACE. Through searching the cis element database (Higo et al., 1999), the promoter was found to be rich in several canonical sequences present in seed storage protein genes: 10 CAAT boxes, 3 (CA)n elements (CNAACAC), 26 E box elements (CANNTG), 1 napin motif (TACACAT), and 5 RY repeats (CATGCA). In addition, 2 ABRE motifs, 11 G-boxes (CACGTG/NACGTN, perfect/imperfect, and 9 DPBF elements (ACACNNG) were also identified. LEA proteins are historically considered to be associated with embryo maturation and seed desiccation that occur late in seed development. The occurrence of BnLEA3-1 expression in the preceding phase of seed development when storage protein genes are most active might be orchestrated by the cis elements found in common with seed storage protein genes.

BnLea3-1 Promoter is Predominantly Functional in Seeds, and is Active in Canola, Tobacco and Pea A 1561-bp segment of the BnLea3-1 promoter (FIG. 6) (SEQ ID NO: 2), retrieved by PCR, was fused to the coding region of *E. coli* GUS gene and the chimeric gene (hereafter BnLEA3-1:: GUS) was introduced into *B. napus* and tobacco by *Agrobacterium tumefaciens*-mediated transformation. Twenty independent transgenic lines from *B. napus* and 10 lines from tobacco showed GUS activity in developing seeds but not in leaf tissues. As shown for one line from each species (Line 9714-22 from canola and 9714-15 from tobacco), a strong GUS-mediated histochemical staining was observed in developing and mature seeds of both canola and tobacco whereas only a weak reaction was seen in imbibed seeds or seedlings (FIG. 7A). Particle bombardment of the above gene construct into pea tissue resulted in GUS expression in seeds but not leaves. Quantitative assay with canola and tobacco samples confirmed that the 1561-nt promoter region of BnLEA3-1 conferred seed-specific expression. Furthermore, the promoter was found to become active in both species in approximately the second phase of the seed development regime and to remain so until seed maturity. This agreed well with the northern results reported above. Notably, the promoter was much more effective, especially in tobacco, than a duplicated CaMV35S promoter that has a very high level constitutive activity (Datla et al., 1992); Furthermore, the BnLEA3-1 promoter activity remained high in mature canola seeds, about 70% of the maximum level that was seen in 40-DAP seeds. In tobacco seeds, however, mature seeds contained only about 20% of the 40-DAP level, but it was still 12-fold greater than the GUS level in CaMV35S seeds. This suggests that BnLEA3-1 promoter is effective for producing foreign proteins in seeds.

BnLEA3-1 Promoter Region Contains Segments that Impact Expression Positively or Negatively in Seeds To examine the presence of possible enhancers and repressors in the promoter region, tobacco was transformed with a series of GUS reporter constructs with nested deletions (FIG. 8). A deletion that retained only 137 nt of the sequence upstream of the TSS (shown as −137 in the abscissa in FIG. 8) promoted a basal GUS activity at 30% of the level seen with the parental construct containing 1561 nt. Interestingly, those constructs with 742 nt, 536 nt, or 301 nt showed greater levels of GUS activity than the parental construct, and −742 construct gave the highest level of GUS activity (710%). In general, the increase in enzyme activity was supported by increased production of GUS protein in the seeds (FIG. 8, inset). The magnitude of expression should be considered in light of the observation that mature seeds of tobacco retained only about 20% of the maximal activity that was seen with younger seeds as shown earlier, thus the level presented here might be an underestimate. These results are likely due to the presence of a dominant silencer function in the sequences upstream of −742 nt. The region downstream of −742 has several positive elements such as ACGTGT (G-box) located at −167, −217, −236, −264, −660, and −682 bp; AACAC located at −167, −183, −214, −657 bp; and CAGTTA located at −248 bp in the region.

Figure 9:
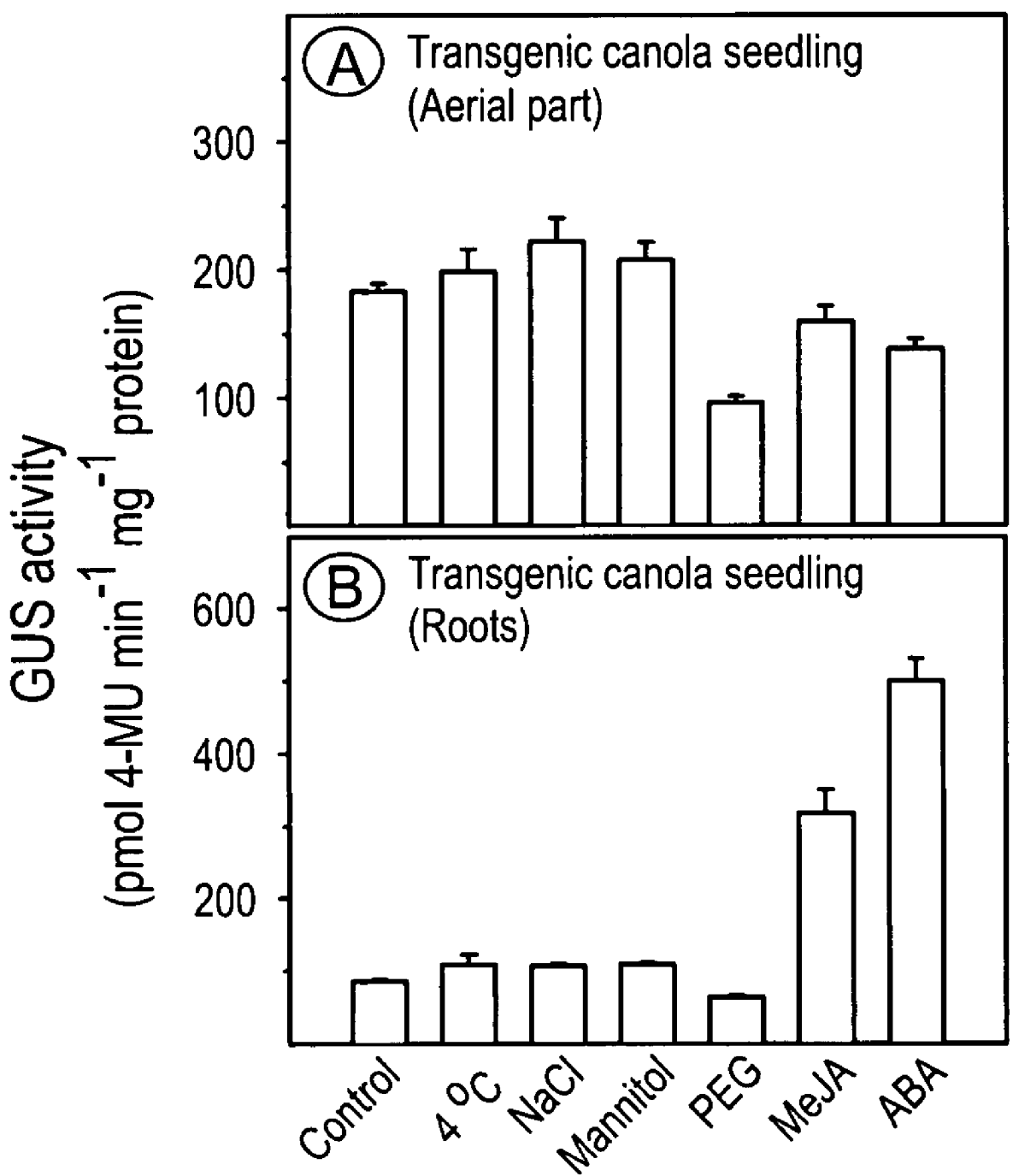
FIG. 9. Analysis of hormonal- and abiotic stress-induced GUS expression in seedlings of *B. napus* transgenic line 9714-22 (see Detailed Description). Panel A, fluorometric GUS enzyme assay of aerial parts of the seedlings (20 d); Panel B, roots only. Panel C, total RNA (15 µg) from whole seedlings in each treatment was fractionated, blotted and hybridized with a PCR-amplified GUS probe. The hybridization signal was measured in a PhosphorImager SI™ (Molecular Dynamics, Inc., Sunnyvale, Calif.) and the signal in control (no stress or chemical treatment) was set at 1 in the relative quantitation.

BnLea3-1 Promoter is Responsive to Abscisic acid (ABA), and Methyl Jasmonate (MeJA) but not to Stress Conditions Expression of BnLEA3-1-like genes was not detectable in seedlings under normal conditions or abiotic stress conditions, but was evident in ABA-treated seedlings as shown above (FIG. 5). To find out specifically if BnLEA3-1 expression would respond to these conditions, a homozygous transgenic line of BnLEA3-1:: GUS was tested for GUS activity (FIG. 9). Cold (4° C.), salinity (NaCl, 150 mM), osmotic stress (mannitol, 150 mM; or 10% v/v polyethylene glycol, PEG) had no positive effect on the promoter activity in shoots or roots, whereas a negative effect on gene expression was seen with PEG. Interestingly both MeJA and ABA enhanced gene expression in roots, but in shoots there was a marginal reduction in GUS activity. This indicated that the basal level of BnLEA3-1 promoter in vegetative tissue under these conditions was weak and that induction by the hormones was very moderate in relation to tile GUS activity levels seen in seeds.

Understanding gene functions that are associated with seed maturation is quite important from fundamental and applied perspectives. We have characterized a gene family specifying LEA proteins in *B. napus*, a major crop cultivated for its seeds. LEA proteins occur widely in all higher plants, and the presence of a LEA-like protein in an alga, point to an ancient function that has been adopted for seed-based perpetuation of plants. There is tremendous structural diversity between and within groups of LEA proteins, and the physiological and developmental contexts in which they manifest also vary. A collective feature of these genes is their up-regulation by abiotic stress conditions, endogenous conditions of a maturing seed and ABA treatment. BnLEA3-1 differed in this respect. Its expression was responsive to developmental aspects of seeds but not to abiotic stress in vegetative tissues. Nor was it as responsive to ABA as other Group 3 LEA genes such as are barley HVA1 (Straub et al., 1994) or wheat Group Lea gene (Ried and Walker-Simmons, 1993). Thus, BnLEA3-1 expression is largely seed-specific. Indeed this property may be quite useful in molecular farming applications. The full-length promoter was superior to enhanced CaMV35S promoter in producing the test protein (GUS) in seeds, and the identification of shorter promoters that afforded even greater levels of transgene expression would be particularly useful in this regard. The observation that the promoter was functional in representatives of three different plant families shows that the cis elements are recognized across the species and that the promoter may be used in a wide range of plants. The weak ABA inducibility in vegetative tissue may be exploited for early identification of potentially high-expressing transgenic lines among those exhibiting a range of transgene expression later in maturing seeds.

Figure 10:
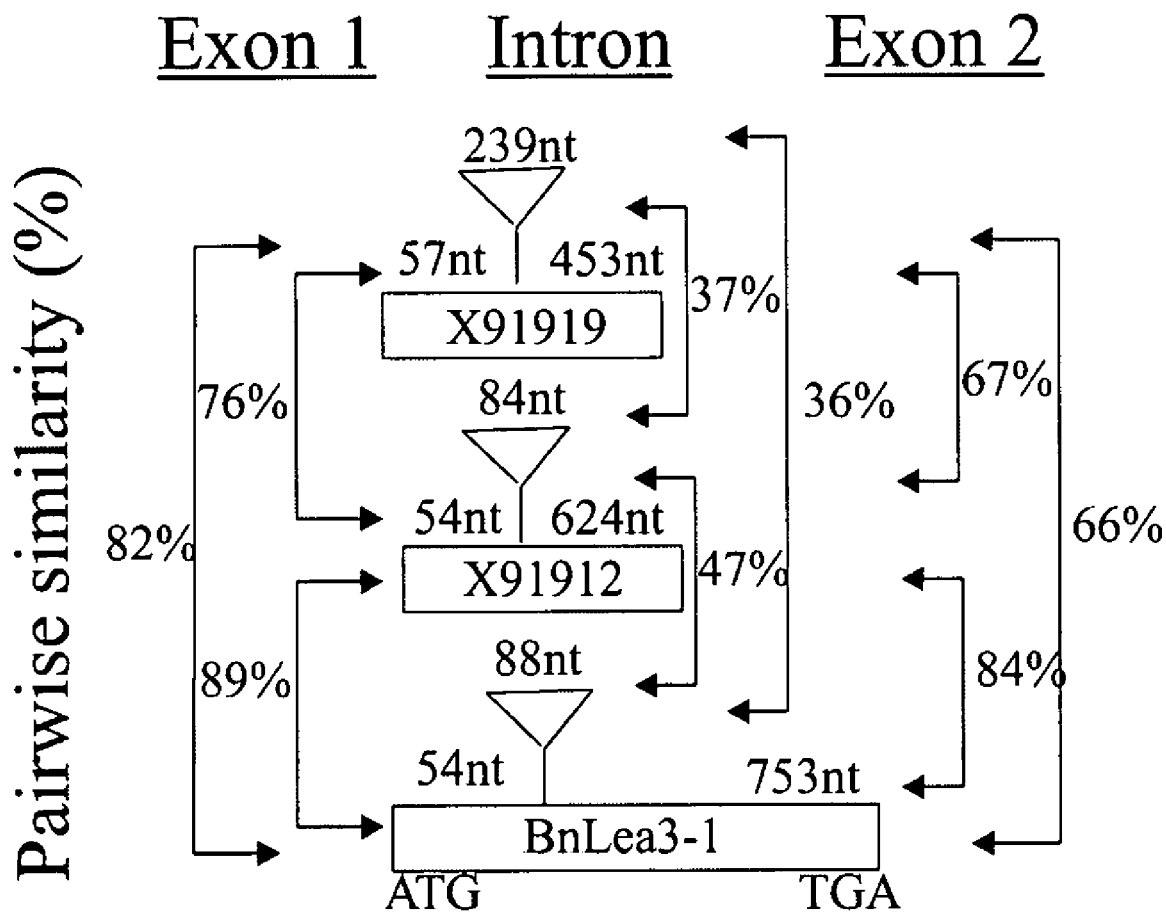
FIG. 10. Pairwise similarity comparison between exons and introns in the coding region of BnLea3-1 and two *Arabidopsis* orthologs.

Group 3 LEA genes from *B. napus* and orthologs from *Arabidopsis* are closely related regarding the position of first exon and intron (FIG. 10). Further analysis reveals the rigidity of the first exon and intron exist among several Group 3 LEA proteins including barley HVA1 and carrot Dc3 (FIG. 3). The rigidity is better described as 18iX pattern where the intron is conserved after the first 18 or so aa residues of the first exon, whereas the second exon is quite variable (X).

Analysis of 23 Group 3 Lea proteins from different species demonstrate that the number of 11-mer repeats vary from 3 in *Corylus avellana* (accession number CAC39110) to 18 in *Glycine max* (accession number S61426). Two to six 11-mer repeats are truncated from BnLea3-1 and *Arabidopsis* orthologs, in comparison with Lea76. Previously it has been reported that sequence variation among Group 1 Lea members from barely is associated with the number of the repeated internal motifs (Stacy et al., 1995). Although the amino acid (aa) consensus is largely conserved at various positions in the 11-mer repeats, several substitutions of consensus aa residues were found throughout the coding region. For example, it is less conserved for the residue K at the 6th position in BnLea3-1 with the second common residue Q having a 36% occurrence (FIG. 1A). Replacing the positively charged K with a polar, uncharged Q may imply some implications for the structure-function relations of BnLea3-1. The occurrence of T/A consensus at position 1 in the 11-mer repeats of BnLea3-1 is unusually high, compared with the consensus in 205 repeats of 22 Group 3 Lea cDNAs. BnLea3-1 and BnLea3-3 differ from BnLea3-2 and BnLea3-4 as well as other Group 3 LEA proteins in that they contain a hydrophobic C-terminus (FIG. 1B). Collectively, these data clearly show that BnLea3-1 is a novel Group 3 Lea gene regarding gene structure and expression transcription pattern.

Both BnLea3-1 and Dc3 promoters are highly seed specific. GUS activity of seed to leaf ratio in transgenic plants carrying BnLea3-1:: GUS is 650 and in Dc3:: GUS is 796. Both BnLea3-1 and Dc3 promoters are also inducible by ABA and to a lesser extent, by MeJA. However, BnLea3-1 promoter differs from Dc3 and HVA1 promoters in that the later two are highly responsive to ABA and osmotic stress but the former is not.

Transcriptional regulation of gene expression is attributed to the cis-acting elements in the upstream promoter region (Datla et al., 1997). Conserved cis-acting elements such as the G-box (Mundy et al., 1990), ABRE (Shen and Ho, 1995), DRE (Yamaguchi-Shinozaki and Shinozaki, 1994), LTRE (Weretilnyk et al., 1993) and other unique sequences (Kao et al., 1996) are found in the promoter region of ABA- and stress-inducible genes. BnLea3-1 promoter contains several conserved G-box like motifs, ABRE elements and DPBF elements (FIG. 6B). These elements may interact with certain transcription factors to modulate ABA-induced gene expression (Datla et al., 1997). However, BnLea3-1 promoter was only weakly inducible by the ABA treatment, this may be due to the lacking of CEI elements (TGCCACCGG) which are required for high ABA responsiveness (Shen and Ho, 1995).

Both BnLea3-1 and BnLea3-2 contains similar cis-elements conserved in other seed storage protein genes including the (C/A)ATGCATG motif or RY element (Dickinson et al., 1988) and the CACA sequence motif in many seed-expressed genes such as lectins and trypsin inhibitors of legumes (Goldberg, 1986). Two CACA box-like motifs (AA-CACA, TACAACA) reside within −170 bp upstream the first transcription start site of BnLea3-1 promoter. This (CA)n element (B-box) conserved among of *B. napus* 2S promoters enhances embryo-specific transcription and represses transcription in endosperm and leaf tissue by interacting with protein factors present in the developing seeds (Rask et al., 1998).

Progressive deletions from the 5' upstream of the BnLea3-1 promoter revealed possible positive elements enhancing GUS transcription residing between −137 bp and −742 bp of the promoter region while negative elements suppressing GUS transcription are located between −742 bp and −1561 bp (FIG. 8). The proximal promoter of sunflower helianthinin gene HaG-3 confers a seed-specific induction by ABA (Nunberg et al, 1994). In contrast, basal ABA-induced GUS expression was found in leaves of the deletion line carrying the −137 bp segment, which comprises a putative TATA box, a perfect (CA)n element, and a perfect G-box.

Although it is slightly activated in vegetative tissues by MeJA and ABA, BnLea3-1 promoter is not activated under osmotic stress or cold treatments. This is an unusual observation not found for other Lea and Lea-like genes (Yamaguchi-Shinozaki and Shinozaki, 1994). Recently Swiatek et al (2002) have reported that ABA and jasmonic acid (JA) negatively regulate cell cycle progression at differential levels. At 200 µM, ABA arrests cell cycle at G1-S phase transition while 100 µM JA arrests cell cycle at both G1-S and G2-M stages in synchronized tobacco BY-2 cells. Given that BnLea3-1 is involved in MeJA and ABA signaling, it seems that it is responsible for cell cycle arrest so the precocious germination can be prevented. On the contrast, another Group 3 member BnLea3-2 whose promoter is active only in seeds, but not in seedlings treated with ABA, MEJA or various stresses (FIG. 11). Regarding ABA- or dehydration-induced expression, BnLea3-2 promoter resembles that of DC8 gene (Hatzopoulos et al., 1990). Therefore, we speculate that BnLea3-2 is likely involved in maintaining proper embryo development probably as ion sequestration proteins in maturing embryos (Dure 1993a, 1993b). Taken together, our data indirectly supports the notion that Group 3 Lea proteins render diverse functions to ensure proper embryo/seed development.

At least two distinct pathways are proposed for ABA-induced gene expression (Li et al., 1999). One is the constitutive ABA signaling pathway in which some RAB (responsive to ABA) and dehydrin genes are involved. Another is tissue-specific signaling pathway involving *Arabidopsis* ABI3, maize C1, and sunflower HaG3 and Ha ds10 (Prieto-Dapena et al., 1999) whose expression is up regulated by ABA only in seeds. Like Dc3, apparently BnLea3-1 is involved in both the constitutive ABA-signaling and the MeJA-signaling pathway. Little is known about the cross-talk details of these signaling cascades. Unraveling the components of the signaling cascades such as protein factors and interacting cis-elements in the promoter region of BnLea3-1 awaits further investigations.

The BnLEA3-2 (9715-22) Promoter is Specifically Active in Maturing Seeds of Transgenic *Brassica napus* as Assayed by the GUS Reporter Expression Method:

The chimerical BnLEA3-2 (9715-22) promoter:GUS was constructed and transformed into *Brassica napus* by the *Agrobacterium*-mediated approach. Detection of GUS activity in the transgenic plants was carried out using 5-bromo-4-chloro-3-indolyl glucuronide (X-GLUC) (Biosynthesis) as described by (Jefferson, 1987). Vegetative tissues, flowers and seeds, dissected if necessary, were incubated in 100 mM sodium phosphate buffer (pH 7.0) with 10 mM EDTA, 0.1% Triton™ X-100, 0.5 mM potassium ferricyanide, 0.5 mM potassium ferrocyanide, and with 1 mM X-GLUC (dissolved in DMSO) at 37° C. overnight. Samples were further cleared by overnight incubation in 70% ethanol. The results were taken into digital photos.

Figure 12:
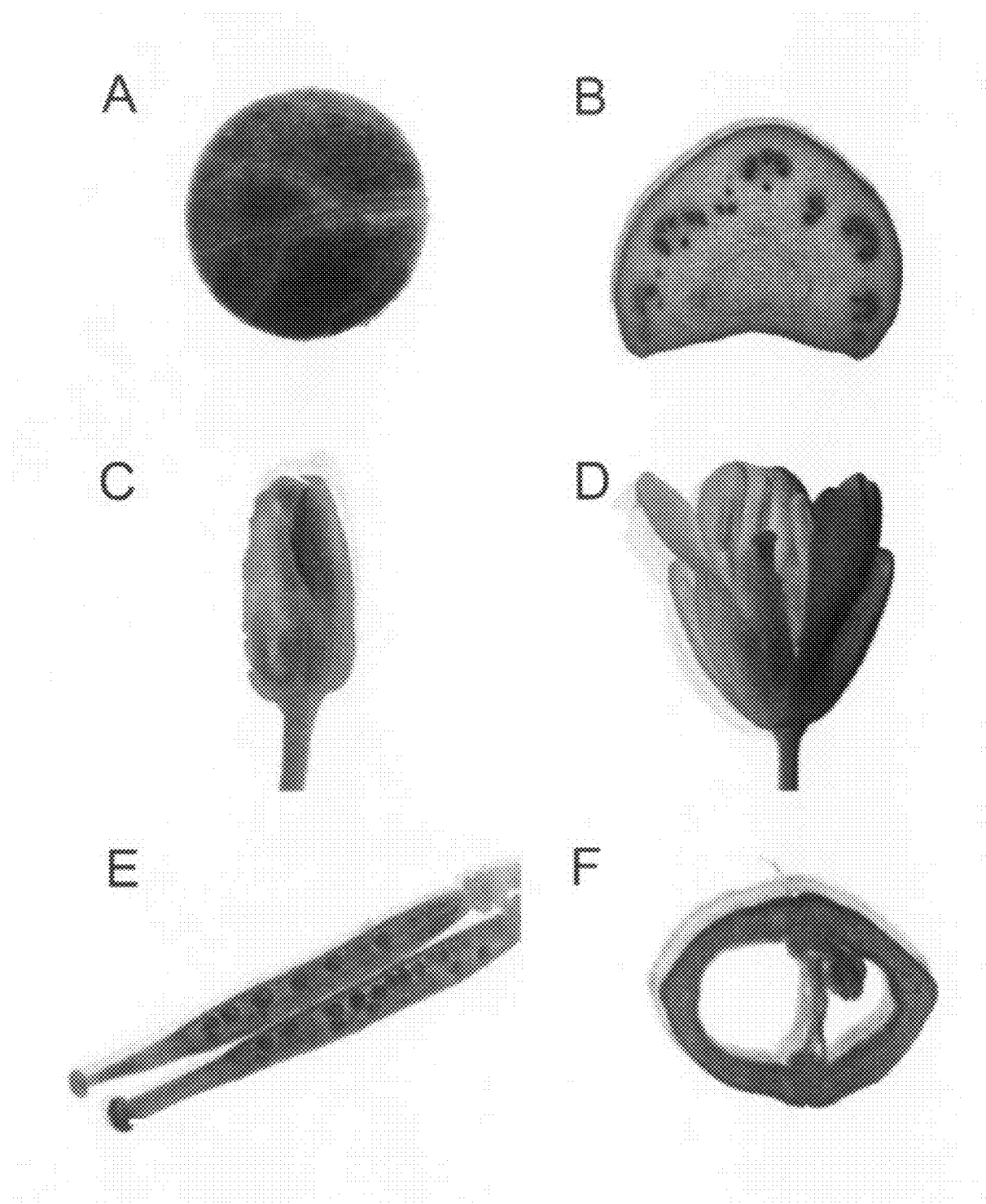
FIG. 12. BnLEA3-2 promoter directed GUS expression was not detectable in the leaf (A), petiole (B, cross section), floral bud (C), flower including carpel, stamen, petal and sepal (D), young siliques including ovules (E), or silique wall (F, cross section). All bars=2 mm.

Results:

1. No positive reaction was detected in vegetative tissue (such as leaf, petiole), floral buds, flowers including anthers, petals and sepals, young siliques including ovules and silique wall (FIG. 12).

Figure 13:
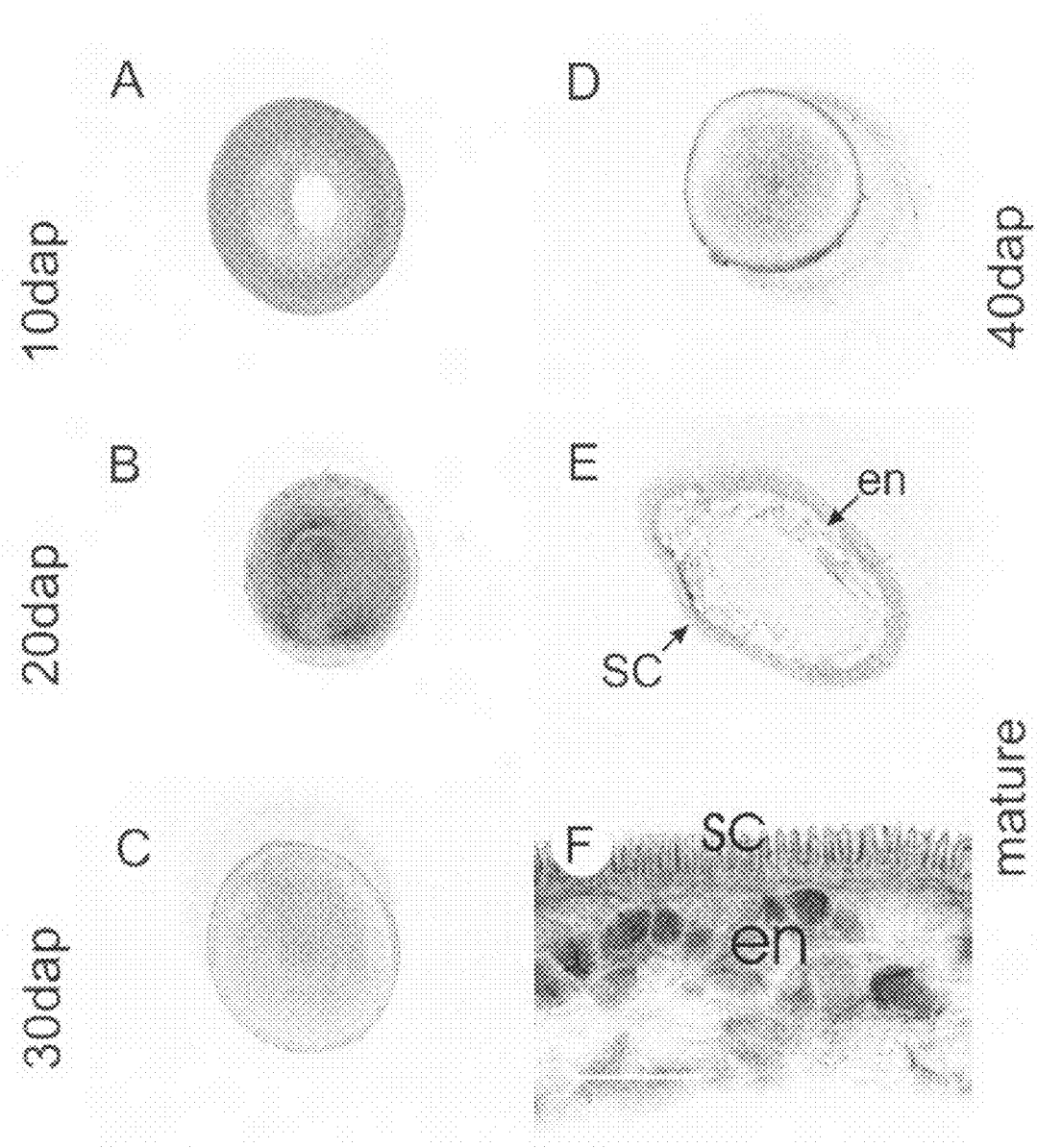
FIG. 13. GUS expression was detected in embryo covering tissue at late stages of seed development. No GUS activity was observed in 10 dap (days after pollination) or 20 dap seed-coat (A and B); weak reaction was found in 30 dap and strong reaction in 40 dap and mature seed-coat (C, D and E); F, a close-up view of mature seed-coat showing GUS activity localized in the endosperm (aleurone). Bar=2 mm (A to D), 1 mm (E) and 0.1 mm (F).

2. GUS activity was detected in embryo tissue at later stages of seed development. It started at 30 DAP (days after pollination) until to mature seeds (FIG. 13) Microphotograph shows that some activity was in the endosperm (aleurone layer).

Figure 14:
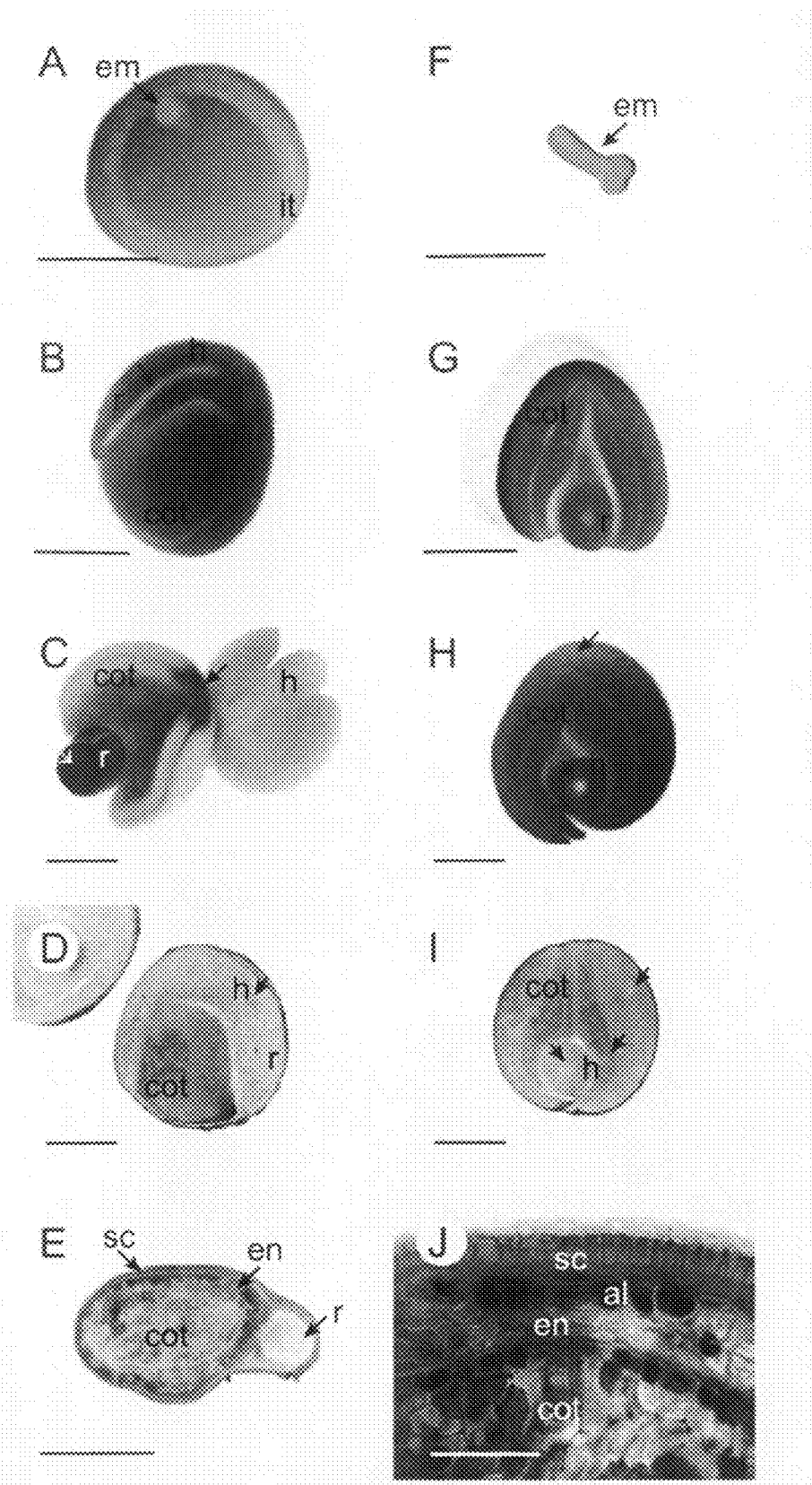
FIG. 14. GUS expression was detected in embryo at late stages of seed development. No GUS activity was observed in young seed coat (A) and embryo (P) at 10 dap. At 20 dap, reaction was limited in the procambium of the radical (B and G). At 30 dap, reaction was observed in the tips of radical, cotyledons (C) as well as procambium (H). At 40 dap, GUS reaction was in the whole embryo although the strongest GUS activity was found in vascular tissue as indicated by arrowheads (D and I). In mature seed, reaction has similar spatial distribution pattern as in 40 dap seed (E and J), em: embryo; it: integument; h: hypocotyls; cot: cotyledons; r: radicle; sc: seed coat; al: aleurone; cn: endosperm; bars=1.0 mm (A to I). 0.1 mm (J).

3. GUS expression was first detected in part of embryo at 20 DAP and then to the whole embryo at the mature stage (FIG. 14). GUS reaction was not detected in the young seed and young embryo. At 20 DAP, the positive reaction was limited in the procambium of both the radicle and the hypocotyl. At 30 DAP, the reaction could be observed in the epidermis of radical and the tips of the cotyledons as well as procambium. After 40 DAP, GUS activity was seen in the whole embryo with the strongest activity in vascular tissue.

Figure 15:
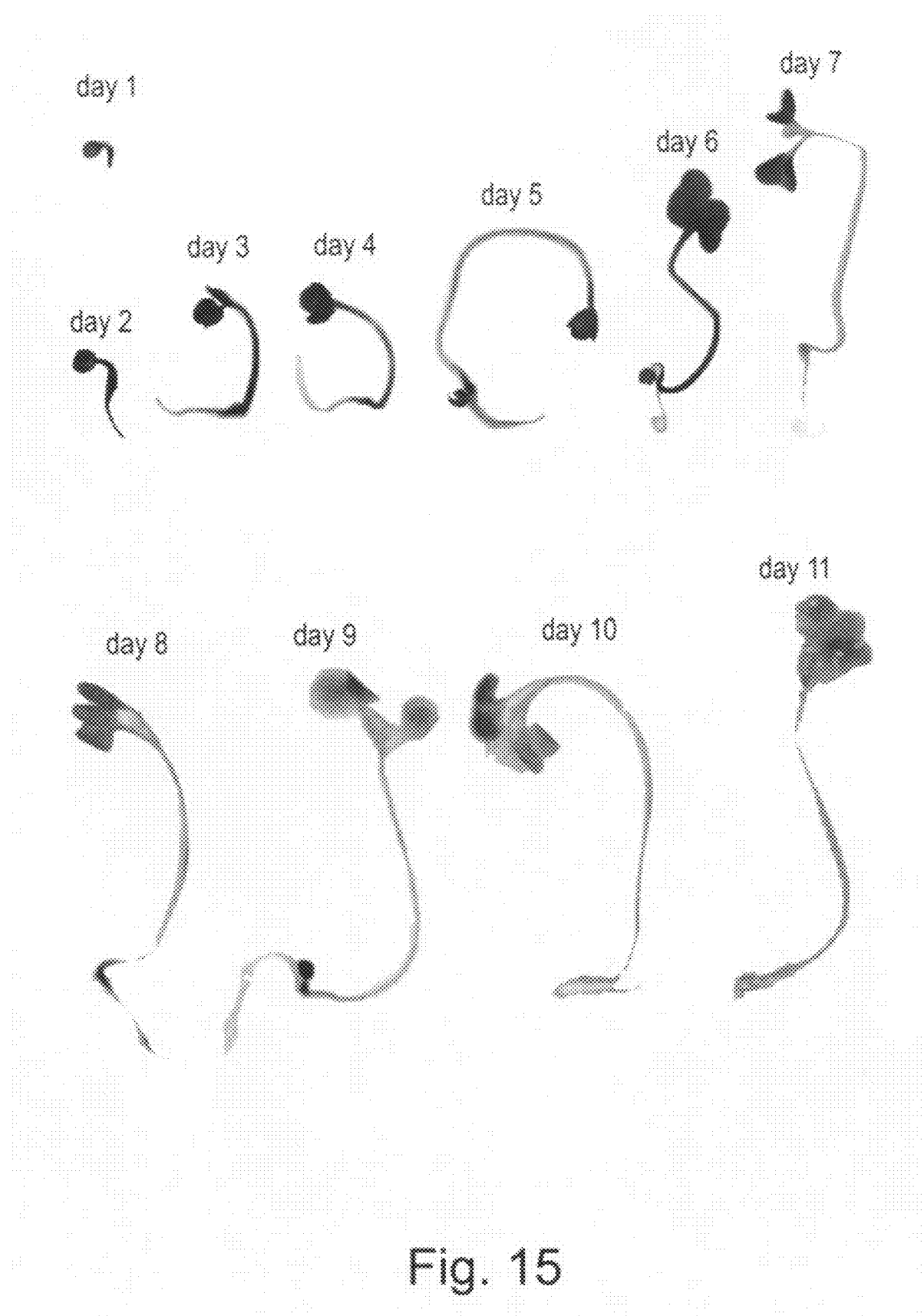
FIG. 15. Decreasing GUS expression during seed germination and at early stages of seedling establishment.

4. GUS expression continued in germinating seeds and young seedling (FIG. 15). Obviously, the activity was reduced from stem, root to cotyledons. After 10 days, virtually no activity could be found in seedlings.

Bray E A (1994) Alterations in gene expression in response to water deficit. In AS Basra, ed, Stress-Induced Gene Expression in Plants. Harwood Academic Publishers, Chur, Switzerland, pp 1-23.

Close T J, Fenton R D, Yang A, Asghar R, DeMason D A, Crone D E, Meyer N C, Moonan F (1993) Dehydrin: the protein. In T J Close, E A Bray, eds, Plant Response to Cellular Dehydration during Environmental Stress American Society of Plant Physiologists, pp 104-118.

TABLE 1

Comparison of homology in Exon I and Exon II of the coding region of BnLea3-1 and other LEA 3 proteins

| Plant | Gene | Accession No. | Alignment of aa residues of Exon I* | Exon I homology (%) |
|---|---|---|---|---|
| Canola | BnLea3-1 | AJ535108 | MASNQ_Q_SYKAGETRGKTQ | 100 |
| | BnLea3-2 | AJ535109 | MASNQ_Q_SYKAGETRGKTQ | 100 |
| | BnLea3-3 | AJ535110 | MASNQ_Q_SYKAGETRGKTQ | 100 |
| | BnLea3-4 | AJ535111 | MASNQ_Q_SYKAGETRGKTQ | 100 |
| Arabidopsis | Type 1 lea 3 | X91912 | MASNQ_Q_SYKAGETRGKAQ | 95 |
| | Type 2 lea 3 | X91919 | MASHQEQ_SYKAGETRGKAQ | 90 |
| Carrot | Lea 3 | A61044 | MASHQDQ_SYKAGEPKGHAQ | 79 |
| Barley | HVA1 | P14928 | MASNQNQGSYHAGETKARTE | 65 |
| Wheat | Lea 3 | X56882 | MASNQNQASYHAGETKARNE | 65 |
| | | AF139915 | MASNQNQASYAAGETKARTE | 65 |
| Chickpea | Lea 3 | AJ224518 | MASHD_Q_SYKAGETMGRTE | 63 |
| Soybean | Lea 3 | AF117884 | MASHR_Q_SYEAGQTKGRTE | 61 |
| Rice | OSLEA3 | AF046884 | MASHQDQASYRAGETKAHTE | 60 |
| | | S52642 | MASQQERASYHAGETKARAE | 55 |
| Cotton | Lea 3 | P13939 | MASHE_Q_SYKAGRAEGRAH | 56 |
| Maize | Lea 3 | Q42376 | MASHQDKASYQAGETKARTE | 55 |

| Gene | Accession No. | No. of 11-mer repeats in Exon II | Exon II homology (%)** | Exon II length (aa) | Reference |
|---|---|---|---|---|---|
| BnLea3-1 | AJ535108 | 11 | 100/100 | 251 | This study |
| BnLea3-2 | AJ535109 | 10 | 80/80 | 144 | This study |
| BnLea3-3 | AJ535110 | 13 | 75/74 | 263 | This study |
| BnLea3-4 | AJ535111 | 6 | 68/61 | 180 | This study |
| Type 1 lea 3 | X91912 | 10 | 82/82 | 208 | NA |
| Type 2 lea 3 | X91919 | 6 | 65/44 | 151 | NA |
| Lea 3 | A61044 | 6 | 44/33 | 144 | Seffens et al (1990) |
| HVAL | P14928 | 10 | 42/39 | 193 | Straub et al (1994) |
| Lea 3 | X56882 | 10 | 40/37 | 204 | Curry et al (1991) |
| | AF139915 | 8 | 44/37 | 159 | NA |
| Lea 3 | AJ224518 | 9 | 50/38 | 159 | Romo et al (2001) |
| Lea 3 | AF117884 | 6 | 46/34 | 122 | Chow et al (1999) |
| OSLEA3 | AF046884 | 8 | 44/42 | 180 | Chen and Chen (1996) |
| | S52642 | 9 | 36/35 | 194 | Takahashi et al (1994) |
| Lea 3 | P13939 | 5 | 48/34 | 118 | Baker et al (1988) |
| Lea 3 | Q42376 | 11 | 39/38 | 201 | White and Rivin (1995) |

*Only the first 18 to 20 aa residues exhibiting high homology were presented in case the intron position was unknown (non-highlighted values). The 16 sequences are listed as SEQ ID NOS: 4-19.
**Individual proteins were compared with whole/partial Exon II aa of BnLea3-1 using the Exon II aa of other Lea 3 proteins.
NA, not applicable.

REFERENCES

Baker J, Steele C, Dure L III (1988) Sequence and characterization of 6 Lea proteins and their genes from cotton. *Plant Mol Biol.* 11:277-291.

Baretls D, Singh M, Salamini F (1988) Onset of desiccation tolerance during development of the barley embryo. *Planta.* 175:485-492.

Busk P K, Pages M (1998) Regulation of abscisic acid-induced transcription. *Plant Mol Biol.* 37:425-435.

Close T J (1997) Dehydrins: a commonalty in response of plants to dehydration and low temperature. *Physiol Plant* 100:291-296.

Creelman R A, Mullet J E (1995) Jasmonic acid distribution and action in plants: Regulation during development and responses to biotic and abiotic stress. *Proc Natl Acad Sci USA.* 92:4114-4119.

Cutler A J, Krochko J E (1999) Formation and breakdown of AB3A. *Trends Plant Sci.* 4:472-478.

Cuming A C (1984) Developmental regulation of gene expression in wheat embryos. Molecular cloning of a DNA sequence encoding the early-methionine-labelled (Em) peptide. *Eur-J-Biochem.* 145:351-357.

Grzelczak Z F, Sattolo M H, Hanley-Bowdoin L K, Kennedy T D, Lane B G (1982) Synthesis and turnover of proteins and mRNA in germinating wheat embryos. *Can J Biochem.* 60:389-397.

Datla R S S, Hammerlindl J K, Panchuk B, Pelcher L E, Keller W A (1992) Modified binary plant transformation vectors with the wild-type gene encoding NPTII. *Gene* 122:383-384.

Datla R, Anderson J W, Selvaraj G (1997) Plant promoters for transgene expression. *Biotechnol. Annu Rev.* 3:269-296.

Davies W J, Jones H G (1991) Abscisic acid: Physiology and Biochemistry. Bios Scientific Publishers, Oxford, UK.

Delseny M, Bies-Etheve N, Carles C, Hull G, Vicient C, Raynal M, Grellet F, Aspart L (2001) Late embryogenesis abundant (LEA) protein gene regulation during *Arabidopsis* seed maturation. *J Plant Physiol.* 158:419-427.

Dickinson C D, Evans R P, Nielson N C (1988) RY repeats in the 5'-flanking region of legume seed protein genes. *Nucl Acids Res.* 16:371.

Dure L III, Crouch M, Harada J, Ho T H D, Mundy J, Quatrano R, Thomas T, Sung Z R (1989) Common amino acid sequence domains among the LEA proteins of higher plants. *Plant Mol Biol.* 12:475-486.

Dure L III (1993a) A repeating 11-mer amino acid motif and plant desiccation. *Plant J.* 3:363-369.

Dare L III (1993b) The Lea proteins of higher plants. In DPS Verma, ed, *Control of Plant Gene Expression.* CRC Press, Boca Raton, Fla., pp 325-335.

Dure L III (1997) Lea proteins and desiccation tolerance of seeds. In B A Larkins, I K Vasil, eds, *Cellular and Molecular Biology of Plant Seed Development.* Kluwer Academic Press, Dordrecht/Boston/London, pp 525-543.

Espinosa-Ruiz A, Belles J M, Serrano R, Culianez-Macia F A (1999) *Arabidopsis thaliana* AtHAL3: a flavoprotein related to salt and osmotic tolerance and plant growth. *Plant J.* 20:529-539.

Goldberg R B (1986) Regulation of plant gene expression. *Phil Trans R Soc Lond B.* 314:343-353.

Goldberg R B, Barker S J, Perez-Grau L (1989) Regulation of gene expression during plant embryogenesis. *Cell.* 56:149-160.

Imai R, Chang L, Ohta A, Bray E A, Takagi M (1996) A lea-class gene of tomato confers salt and freezing tolerance when expressed in *Saccharomyces cerevisiae. Gene.* 170: 243-248.

Harada J J, DeLisle A J, Baden C S, Crouch M L (1989) Unusual sequence of an abscisic acid-inducible mRNA which accumulates late in *Brassica napus* seed development. *Plant Mol Biol.* 12:395-401.

Hays D B, Wilen R W, Sheng C X, Moloney M M, Pharis R P (1999) Embryo-specific gene expression in microspore-derived embryos of *Brassica napus.* An interaction between abscisic acid and jasmonic acid. *Plant Physiol.* 119:1065-1072.

Higo K, Ugawa Y, Iwamoto M, Korenaga T (1999) Plant cis-acting regulatory DNA elements (PLACE) database: 1999. *Nucl Acids Res.* 21:297-300.

Hsing Y C, Tsou C H, Hsu T F, Chen Z Y, Hsieh K L, Hsieh J S, Chow TY (1998) Tissue- and stage-specific expression of a soybean (*Glycine max* L.) seed-maturation, biotinylated protein. *Plant Mol Biol.* 38:481-490.

Ingram J, Bartels D (1996) The molecular basis of dehydration tolerance in plants. *Annu Rev Plant Physiol Plant Mol Biol.* 47:377-403.

Jain R K, Selvaraj G (1997) Molecular genetic improvement of salt tolerance in plants. *Biotech Annu Rev.* 3:245-267.

Jefferson R A (1987) Assaying chimeric genes in plants. The GUS gene fusion systems. *Plant Mol Biol Rep.* 5:387-405.

Kao C, Cocciolone S M, Vasil I K, McCarty D R (1996) Localization and interaction of the cis-acting elements for abscisic acid, VIVIPAROUS1, and light activation of the C1 gene of maize. *Plant Cell.* 8:1171-1179.

Lane B G (1991) Cellular desiccation and hydration: developmentally regulated proteins, and the maturation and germination of seed embryos. *FASEB J.* 5:2893-2901.

Leung J, Giraudat J (1998) Abscisic acid signal transduction. *Annu Rev Plant Physiol Plant Mol Biol.* 49:199-222.

Li G F, Bishop K J, Chandrasekharan M B, Hall T C (1999) β-phaseolin gene activation is a two-step process: PvALF-facilitated chromatin modification followed by abscisic acid-mediated gene activation. *Proc Natl Acad Sci USA.* 96:7104-7109.

McCubbin W D, Kay C M (1985) Hydrodynamic and optical properties of wheat germ Em protein. *Can J Biochem.* 63:803-811.

Moons A, De Keyser A, Montagu M V (1997) A group 3 LEA cDNA of rice responsive to abscisic acid, but not to jasmonic acid, shows variety-specific differences in salt stress response. *Gene.* 191:197-204.

Mundy J, Yamaguchi-Shinozaki K, Chua N H (1990) Nuclear proteins bind conserved elements in the abscisic acid-responsive promoter of a rice rab gene. *Proc Natl Acad Sci USA.* 87:1406-1410.

Murashige T, Skoog F (1962) A revised medium for rapid growth and bioassay with tobacco tissue cultures. *Physiol Plant.* 15:473-497.

Nair R B, Joy I V R W, Kurylo E, Shi X H, Schnaider J, Datla R S S, Keller W A, Selvaraj G (2000) Identification of a CYP84 family of cytochrome P450 dependent mono-oxygenase genes in *Brassica napus* and perturbation of their expression for engineering sinapine reduction in the seeds. *Plant Physiol.* 123:1623-1634.

Nunberg A N, Li Z W, Bogue M A, Vivekananda J, Reddy A S, Thomas T L (1994) Developmental and hormonal regulation of sunflower helianthinin gene: proximal promoter sequences confer regionalized seed expression. *Plant Cell.* 6:473-486.

Pammenter N W, Berjak P (2000) Evolutionary and ecological aspects of recalcitrant seed biology. *Seed Sci Res.* 10:301-306.

Prieto-Dapena P, Almoguera C, Rojas A, Jordano J (1999) Seed-specific expression patterns and regulation by ABl3 of an unusual late embryogenesis-abundant gene in sunflower. *Plant Mol Biol.* 39:615-627.

Quatrano R S (1987) The role of hormones during seed development. In *Plant Hormones and Their Role in Plant Growth and Development*, P J Davis ed, Martinus Nijhoff publishers, Boston, pp 494-514.

Quatrano R S, Bartels D, Ho T H D, Pages M (1997) New insights into ABA-mediated processes. *Plant Cell.* 9:470-475.

Rask L, Ellerstrom M, Ezcurra I, Stalberg K, Wycliffe P (1998) Seed-specific regulation of the napin promoter in *Brassica napus. J Plant Physiol.* 152:595-599.

Ried J L, Walker-Simmons M K (1993) Group 3 late embryogenesis abundant proteins in desiccation-tolerant seedlings of wheat (*Triticum aestivum* L.). *Plant Physiol.* 102:125-131.

Rogers S O, Bendich A J (1985) Extraction of DNA from milligram amounts of fresh, herbarium and mummified plant tissues. *Plant Mol Biol.* 5:69-76.

Sambrook J, Fritsch E F, Maniatis A (1989) *Molecular cloning: A Laboratory Manual*, 2nd ed., Cold Spring Harbor Laboratory Press, Cold Spring Harbor, N.Y.

Seffens W S, Almoguera C, Wilde I I D, Haar R A V, Thomas T L (1990) Molecular analysis of a phylogenetically conserved carrot gene: developmental and environmental regulation. *Dev Genet.* 11:65-76.

Shen Q, Uknes S J, Ho T-HD (1993) Hormone response complex of a novel abscisic acid and cyclohexmide inducible barley gene. *J Bio Chem.* 268:23652-23660.

Shen Q, Ho T H D (1995) Functional dissection of an abscisic acid (ABA)-inducible gene reveals two dependent ABA-responsive complexes each containing a G-box and a novel cis-acting element. *Plant Cell.* 7:295-307.

Stacy R A P, Espelund M, Larsen S S, Hollung K, Helliesen E, Jakobsen K S (1995) Evolution of the group 1 late embryogenesis abundant (Lea) genes: analysis of the Lea B19 gene family in barley. *Plant Mol Biol.* 28:1039-1054.

Straub P F, Shen Q, Ho T H D (1994) Structure and promoter analysis of an ABA- and stress-regulated barley gene, HVA1. *Plant Mol Biol.* 26:617-630.

Swiatek A, Lenjou M, Bockstaele D V, Inze D, Onckelen I I V (2002) Differential effect of jasmonic acid and abscisic acid on cell cycle progression in tobacco BY-2 cells. *Plant Physiol.* 128:201-211.

Thomas T L (1993) Gene expression during plant embryogenesis and germination: an overview. *Plant Cell.* 5:1401-1410.

Thomashow M F (1999) Plant cold acclimation: Freezing, tolerance genes and regulatory mechanism. *Annu Rev Plant Physiol Plant Mol Biol.* 50:571-599.

Truco M J, Hu J, Sadowski J, Quiros C F (1996) Inter- and intra-genomic homology of the *Brassica* genomes: implications for their origin and evolution. *Thoer Appl Genet.* 93:1225-1233.

Weretilnyk E, Orr W, Weretilnyk T C, Lu B, Singh J (1993) Characterization of three related low-temperature-regulated cDNAs from winter *Brassica napus*. *Plant Physiol.* 101:171-177.

Wolkers W F, McCready S, Brandt W F, Lindsey G G, Hoekstra F A (2001) Isolation and characterization of a D-7 LEA protein from pollen that stabilizes glasses in vitro. *Biocliimica-et-biophysica-acta-protein-structure-and-molecular-enzymology.* 1544:196-206.

Yamaguchi-Shinozaki K, Koizumi M, Urao S, Shinozaki K (1992) Molecular cloning and characterization of 9 cDNAs for genes that are responsive to desiccation in *Arabidopsis thaliana*: sequence analysis of one cDNA clone that encodes a putative transmembrane channel protein. *Plant Cell Physiol.* 33:217-224.

Yamaguchi-Shinozaki K, Shinozaki K (1994) A novel cis-acting element in an *Arabidopsis* gene is involved in responsiveness to drought, low-temperature, or high-salt stress. *Plant Cell.* 6:251-264.

The invention claimed is:

1. A promoter comprising an isolated DNA sequence comprising nucleotides 1596 to 1952 of SEQ ID. NO: 1, which selectively promotes gene expression in a plant seed and/or in vegetative tissues for early detection of gene expression.

2. The promoter of claim 1 comprising nucleotides 1361 to 1952 of SEQ ID. NO: 1.

3. The promoter of claim 1 comprising nucleotides 1155 to 1952 of SEQ ID. NO: 1.

4. The promoter of claim 1 comprising nucleotides 336 to 1952 of SEQ ID. NO: 1.

5. A plant, seed, vector, or expression cassette comprising the promoter of claim 1.

6. The plant, seed, vector, or expression cassette of claim 5, wherein the promoter comprises nucleotides 1361 to 1952 of SEQ ID. NO: 1.

7. The plant, seed, vector, or expression cassette of claim 5, wherein the promoter comprises nucleotides 1155 to 1952 of SEQ ID. NO: 1.

8. The plant, seed, vector, or expression cassette of claim 5, wherein the promoter comprises nucleotides 336 to 1952 of SEQ ID. NO: 1.

9. A DNA construct comprising the promoter of claim 1 operably linked to a gene.

10. The DNA construct of claim 9, wherein the promoter comprises nucleotides 1361 to 1952 of SEQ ID. NO: 1.

11. The DNA construct of claim 9, wherein the promoter comprises nucleotides 1155 to 1952 of SEQ ID. NO: 1.

12. The DNA construct of claim 9, wherein the promoter comprises nucleotides 336 to 1952 of SEQ ID. NO: 1.

\* \* \* \* \*